(12) United States Patent
Bachar

(10) Patent No.: US 11,738,184 B2
(45) Date of Patent: Aug. 29, 2023

(54) DILATING DEVICE AND METHOD FOR PROSTATIC URETHRA

(71) Applicant: Butterfly Medical Ltd., Yokneam (IL)

(72) Inventor: Yehuda Bachar, Givaat Shmuel (IL)

( * ) Notice: Subject to any disclaimer, the term of this patent is extended or adjusted under 35 U.S.C. 154(b) by 60 days.

(21) Appl. No.: 17/246,654

(22) Filed: May 2, 2021

(65) Prior Publication Data

US 2021/0290917 A1  Sep. 23, 2021

Related U.S. Application Data

(60) Division of application No. 16/403,632, filed on May 6, 2019, now Pat. No. 11,027,106, which is a continuation-in-part of application No. 15/747,940, filed as application No. PCT/IL2015/050092 on Jul. 26, 2016, now Pat. No. 10,507,122, said application No. 16/403,632 is a continuation-in-part of application No. 15/114,107, filed as application No. PCT/IB2015/055731 on Jul. 29, 2015, now Pat. No. 10,478,283.

(60) Provisional application No. 61/931,645, filed on Jan. 26, 2014.

(51) Int. Cl.
| | |
|---|---|
| *A61F 2/26* | (2006.01) |
| *A61F 2/04* | (2013.01) |
| *A61M 29/02* | (2006.01) |
| *A61B 1/307* | (2006.01) |
| *A61B 18/00* | (2006.01) |

(52) U.S. Cl.
CPC ............ *A61M 29/02* (2013.01); *A61B 1/307* (2013.01); *A61B 2018/00517* (2013.01); *A61F 2002/047* (2013.01); *A61M 2210/1096* (2013.01)

(58) Field of Classification Search
CPC .......... A61M 2210/1096; A61M 29/02; A61F 2002/047; A61B 2018/00517
See application file for complete search history.

(56) References Cited

U.S. PATENT DOCUMENTS

| | | |
|---|---|---|
| 5,269,802 A | 12/1993 | Garber |
| 5,496,365 A | 3/1996 | Sgro |
| 6,994,093 B2 | 2/2006 | Murphy et al. |
| 8,591,569 B2 | 11/2013 | Shin et al. |
| 8,603,187 B2 | 12/2013 | Kilemnick et al. |
| 10,105,132 B2 | 10/2018 | Lamson et al. |
| 2002/0010487 A1 | 1/2002 | Evans et al. |

(Continued)

FOREIGN PATENT DOCUMENTS

| | | |
|---|---|---|
| CN | 106102655 A | 11/2016 |
| WO | 2010073244 A2 | 7/2010 |

(Continued)

OTHER PUBLICATIONS

May 11, 2016 International Search Report issued in International Patent Application No. PCT/IB2015/055731.

(Continued)

*Primary Examiner* — Dinah Baria

(57) ABSTRACT

A dilating device for the prostatic urethra comprising: Prostatic implant includes independently actuatable distal retractor incorporating and proximal retractor. Retractors may be connected via a spine member. System and method include implant manipulator detachably connected to implant, for manipulating and forcing implant into close proximity, for delivery into subject.

16 Claims, 20 Drawing Sheets

(56) References Cited

U.S. PATENT DOCUMENTS

| | | |
|---|---|---|
| 2002/0029075 A1 | 3/2002 | Leonhardt |
| 2003/0040803 A1 | 2/2003 | Rioux et al. |
| 2003/0060870 A1 | 3/2003 | Reever |
| 2003/0069647 A1 | 4/2003 | Desmond et al. |
| 2004/0167635 A1 | 8/2004 | Yachia et al. |
| 2007/0270932 A1* | 11/2007 | Headley .............. A61F 2/95 623/1.11 |
| 2009/0156977 A1 | 6/2009 | Daignault et al. |
| 2010/0137893 A1 | 6/2010 | Kilemnick et al. |
| 2011/0098825 A1 | 4/2011 | Shin et al. |
| 2011/0276081 A1 | 11/2011 | Kilemnik |
| 2014/0012192 A1 | 1/2014 | Bar-On et al. |

FOREIGN PATENT DOCUMENTS

| | | |
|---|---|---|
| WO | 2015101975 A1 | 7/2015 |
| WO | 2015111063 A1 | 7/2015 |

OTHER PUBLICATIONS

May 31, 2015 International Search Report issued in International Patent Application No. PCT/IL2015/050092.
In re Nehrenberg, 47 C.C.P.A. 1159, 126 U.S.P.Q. 383, 280 F.2d 161 (1960) Jul. 6, 1960 ■ United States Court of Customs and Patent Appeals ■ No. 6568 47 C.C.P.A. 1159, 126 U.S.P.Q. 383, 280 F.2d 161.

\* cited by examiner

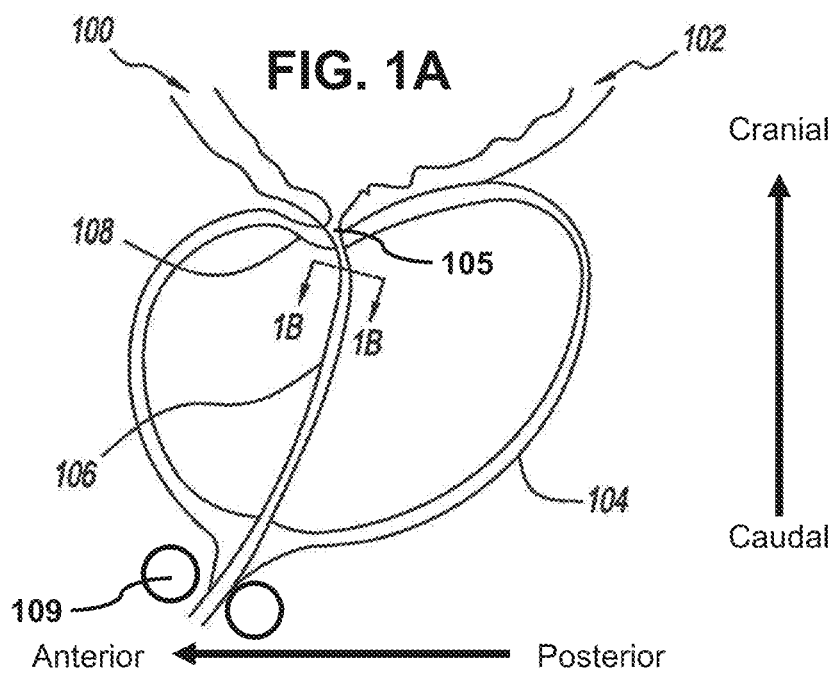
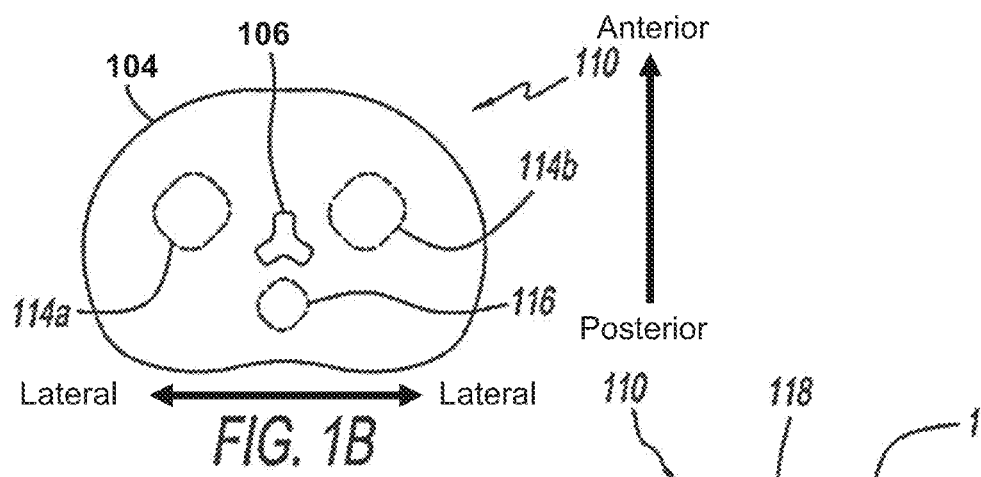
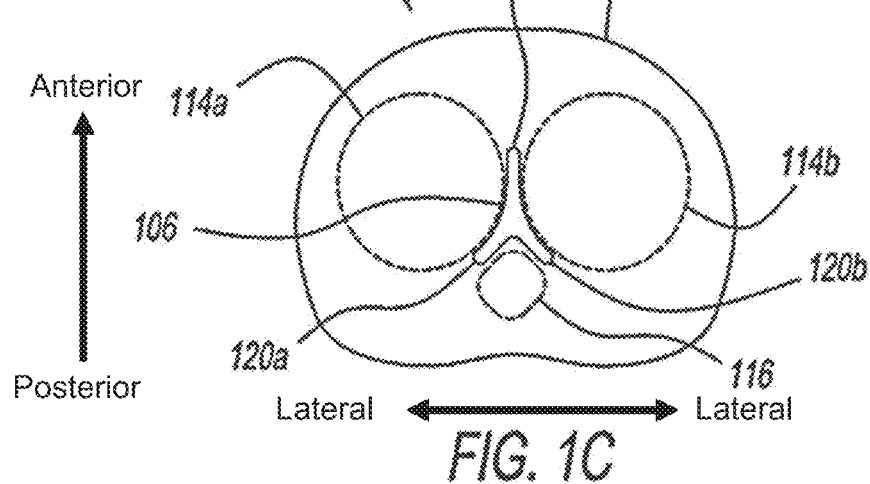

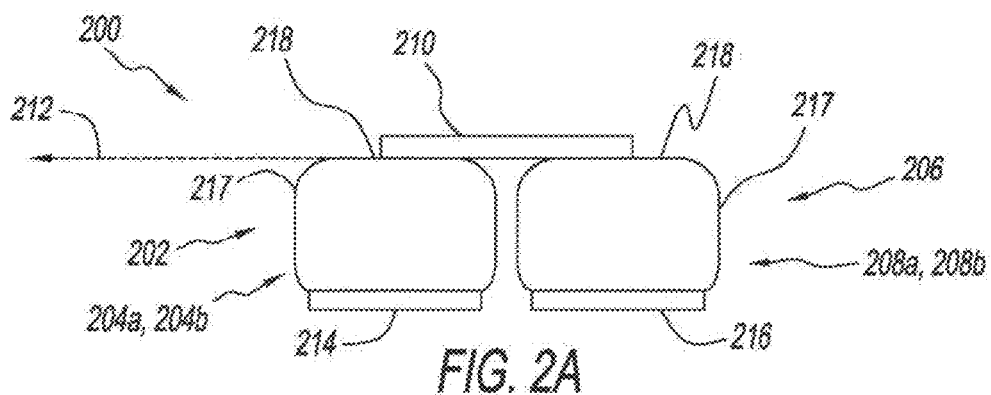
FIG. 2A
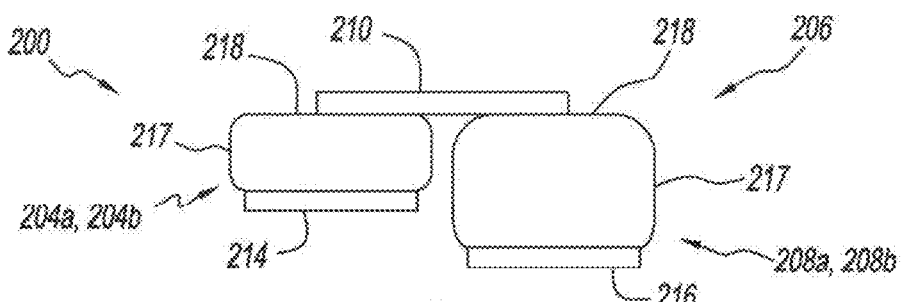
FIG. 2B
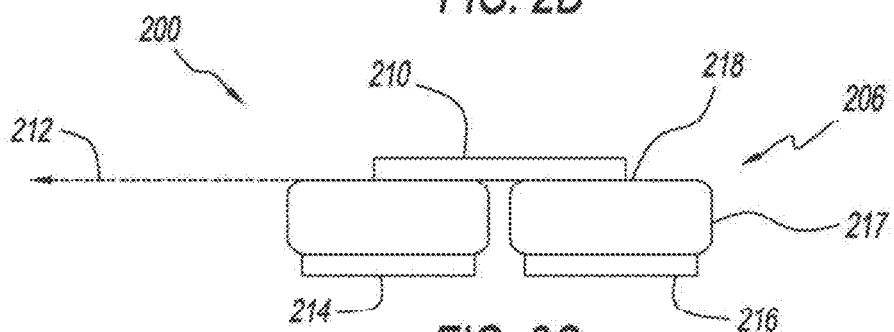
FIG. 2C
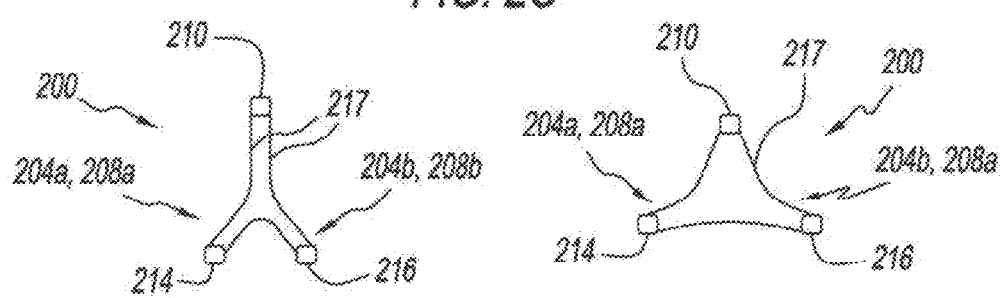
FIG. 2D
FIG. 2E

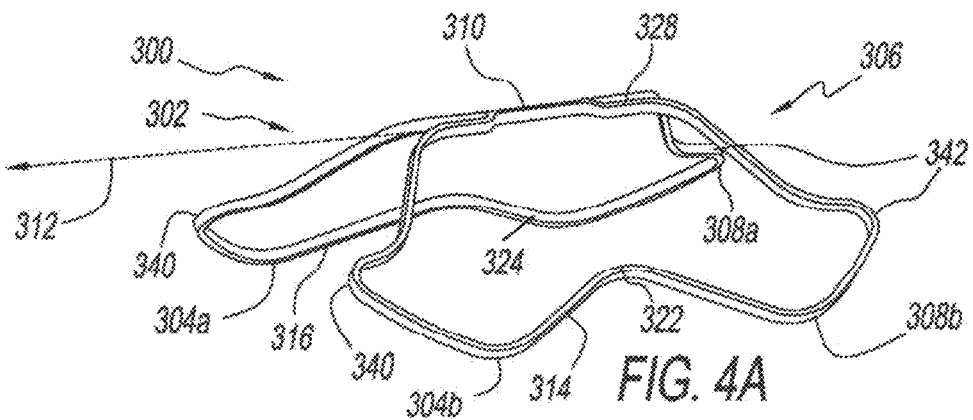
FIG. 4A
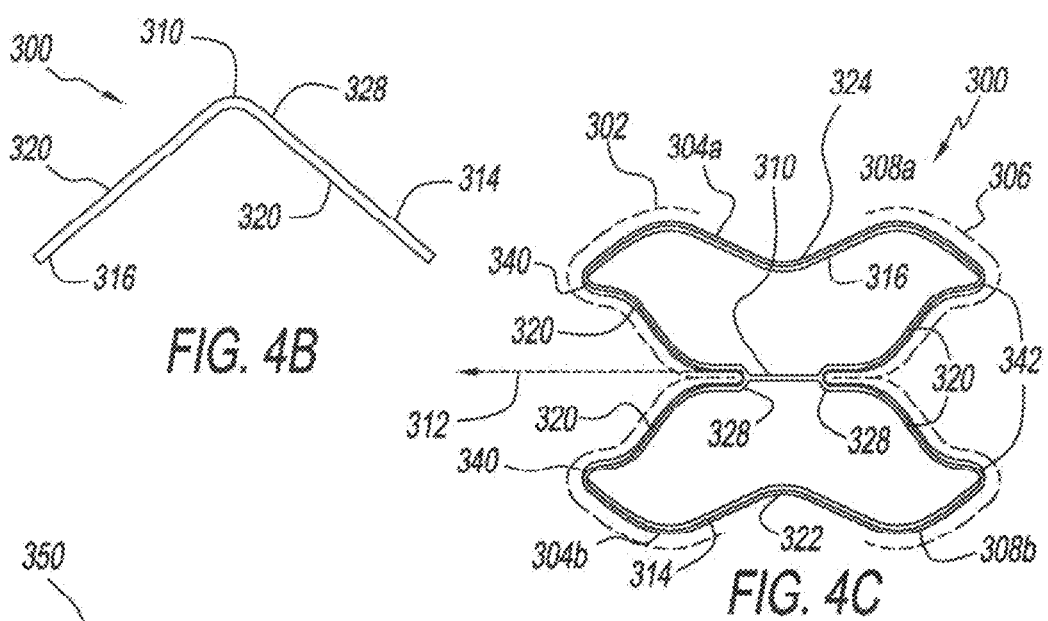
FIG. 4B
FIG. 4C
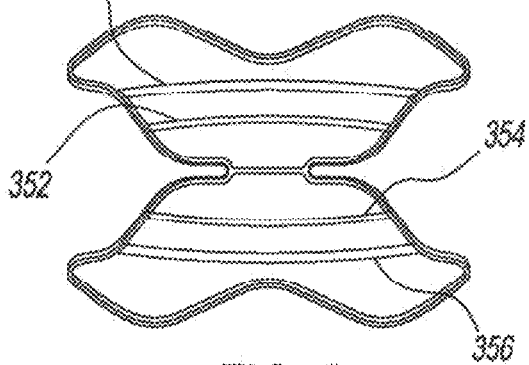
FIG. 5
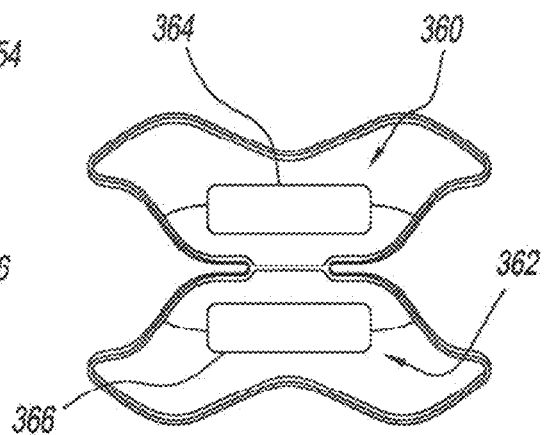
FIG. 6

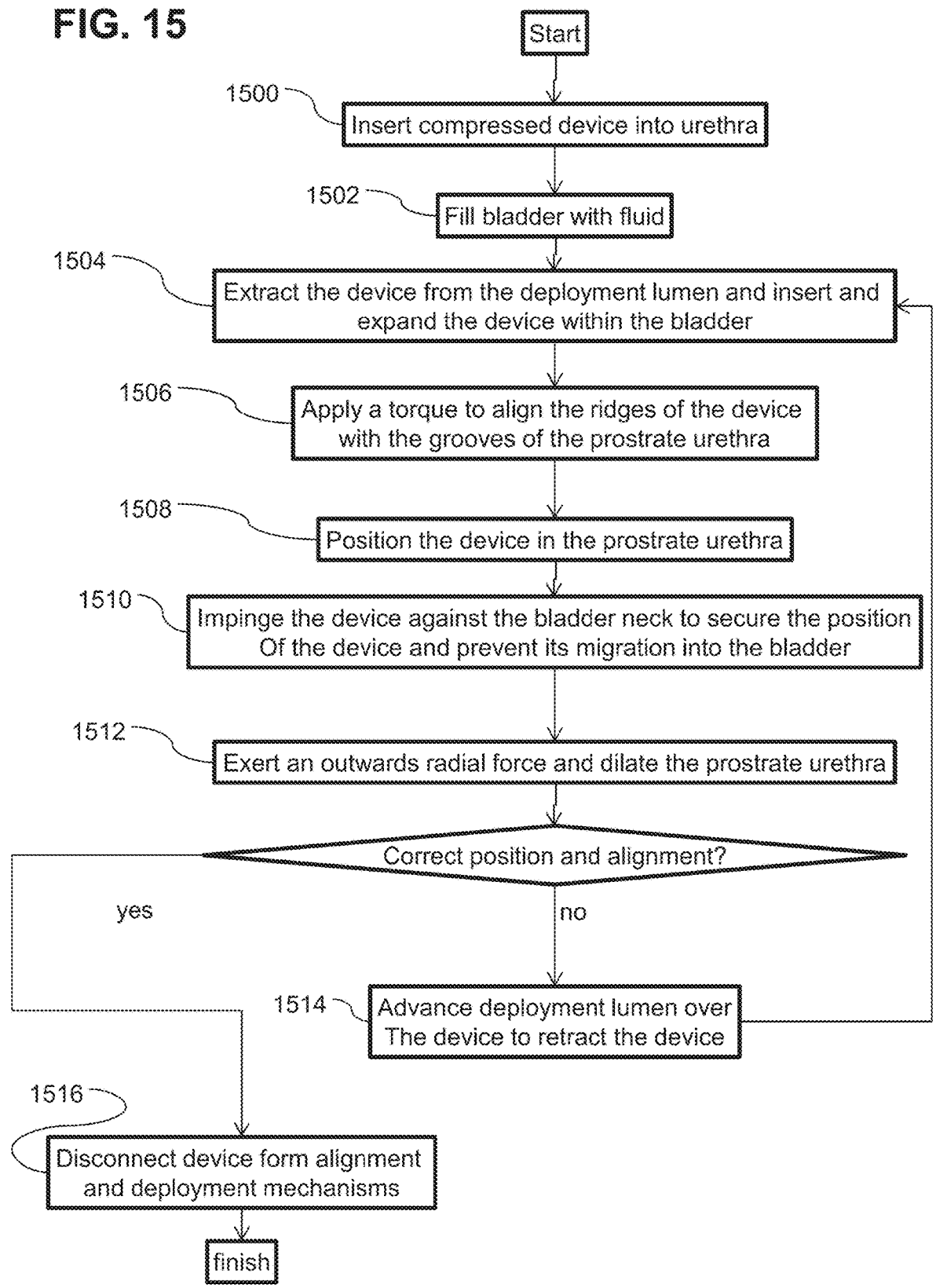

DILATING DEVICE AND METHOD FOR PROSTATIC URETHRA

RELATED APPLICATION/S

This application is a continuation in part of U.S. patent application Ser. No. 15/114,107 filed 26 Jul. 2016 which claims benefits from International Patent Application no. PCT/IL2015/050092 filed 26 Jan. 2015 which claims benefit of U.S. Provisional Patent Application No. 61/931,645, filed Jan. 26, 2014 which claims the benefit of U.S. Provisional Patent Application No. 61/931,645, filed Jan. 26, 2014 and entitled "A Dilating Device for Prostatic urethra" and this application is a continuation in part of U.S. patent application Ser. No. 15/747,940 filed 26 Jan. 2018, which claims benefits from International Patent Application no. PCT/IB2015/055731 filed 29 Jul. 2015.

The contents of the above applications are all incorporated by reference as if fully set forth herein in their entirety.

FIELD OF THE INVENTION

The present invention, in some embodiments thereof, relates to the field of urological medical devices and applications thereof, and more particularly, but not exclusively, to a urological (prostatic) implant, system, and method for retracting or/and supporting periurethral tissue enclosing a prostatic urethra along a length of prostate lobes.

BACKGROUND OF THE INVENTION

The present invention, in some embodiments thereof, relates to the field of urological medical devices and applications thereof, and more particularly, but not exclusively, to a urological (prostatic) implant, system, and method for retracting or/and supporting periurethral tissue enclosing a prostatic urethra along a length of prostate lobes.

Benign prostate hyperplasia (BPH), also known as benign prostatic hypertrophy, is a urological disease in which the prostate enlarges and constricts the urethra. BPH affects a majority of the male population over 50 years of age, and is thus of great medical and commercial importance.

Surgical treatment of hypertrophy of the prostate has been a routine procedure for many years. One method of such surgical treatment is open prostatectomy wherein the gland is totally or partially removed. Another method of surgical treatment is transurethral resection of the prostate (TURP). However, surgical treatment is an extremely invasive procedure which is debilitating, painful and often traumatic to the patient. Various complications including impotence, incontinence, bleeding, infection and other undesirable problems attendant with such surgery can result.

Another procedure to treat prostatic hypertrophy is to place a catheter at the external opening of the urethra and into the obstructed portions of the urethra, allowing urine to pass from the bladder by way of the catheter lumen. These urinary catheters typically employ a positioning or retention balloon at the distal tip which inflates at the bladder neck and prevents the expulsion of the catheter from the body.

Ablation techniques, for example, based on using heat, such as produced by microwave or laser energy, may be provided in combination with such catheters for treating the enlarged portion of the prostate. However, this procedure may result in pain and discomfort to the patient The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

The present invention, in some embodiments thereof, relates to a urological (prostatic) implant system, and method for retracting or/and supporting periurethral tissue enclosing a prostatic urethra along a length of prostate lobes.

According to an aspect of some embodiments of the present invention, there is provided an implant for retracting or/and supporting periurethral tissue enclosing a prostatic urethra along a length of prostate lobes, the implant comprising: a distal retractor incorporating a first and a second craniolateral corners; and a proximal retractor incorporating a first and a second caudolateral corners; wherein said distal retractor and proximal retractor are independently actuatable.

According to some embodiments of the invention, the distal retractor is connected to, or integrally formed as a single structure with, the proximal retractor, via an elongated spine member extending along a spinal longitudinal axis or/and a plurality of elongated edge members.

According to some embodiments of the invention, the distal retractor or/and the proximal retractor are in a form of a pair of curved wing-like structures connected to the spine member via interconnecting members, and symmetrically opposing each other relative to the spinal longitudinal axis.

According to some embodiments of the invention, each the interconnecting members includes at least one elastic portion adjoining the spine member, the elastic portion being non-stressed when a first of the curved wing-like structures in the pair is pivotally positioned centrally away from a second of the curved wing-like structures in the pair about the spinal longitudinal axis, so as to form a predetermined maximal elongated edge member spanning angle. Optionally, the at least one elastic portion exhibits an increase in stress when subjected to a moment of force that pivotally shifts the first curved wing-like structure towards the second curved wing-like structure about the spinal longitudinal axis.

According to some embodiments of the invention, the implant further comprises at least one tissue support member extending between a first elongated edge member and the spinal longitudinal axis, and at least one other tissue support member extending between a second elongated edge member and the spinal longitudinal axis, wherein each tissue support member is sized and configured for supporting a portion of a prostatic lateral lobe when the spine member engages an anterior interlobar groove that extends between prostatic lateral lobes in the prostate, and when the first and second elongated edge members engage corresponding posterolateral interlobar grooves. Optionally, the spine member has a length being equal to or less than length of the anterior interlobar groove or/and substantially less than length of each of the first and second elongated edge members. Optionally, the first elongated edge member is sized for positioning in a left posterolateral interlobar groove that extends between a left prostatic lateral lobe and a prostatic medial lobe, and the second elongated edge member is sized for positioning in a right posterolateral interlobar groove that extends between a right prostatic lateral lobe and the prostatic medial lobe.

According to an aspect of some embodiments of the present invention, there is provided an implant for retracting or/and supporting periurethral tissue enclosing a prostatic urethra along a length of prostate lobes, the implant comprising: an elongated spine member having a spinal longitudinal axis, a first elongated edge member and a second elongated edge member symmetrically opposing each other relative to the spinal longitudinal axis, each elongated edge member is interconnected to the spine member via at least one interconnecting member.

According to some embodiments of the invention, at least one tissue support member extending between the first elongated edge member and the spinal longitudinal axis, and at least one other tissue support member extending between the second elongated edge member and the spinal longitudinal axis, wherein each tissue support member is sized and configured for supporting a portion of a prostatic lateral lobe when the spine member engages an anterior interlobar groove that extends between prostatic lateral lobes in the prostate, and when the first and second elongated edge members engage corresponding posterolateral interlobar grooves.

According to some embodiments of the invention, the spine member has a length being equal to or less than length of the anterior interlobar groove or/and substantially less than length of each of the first and second elongated edge members. Optionally, the first elongated edge member is sized for positioning in a left posterolateral interlobar groove that extends between a left prostatic lateral lobe and a prostatic medial lobe, and the second elongated edge member is sized for positioning in a right posterolateral interlobar groove that extends between a right prostatic lateral lobe and the prostatic medial lobe.

According to some embodiments of the invention, each of the interconnecting members includes at least one elastic portion adjoining the spine member, the elastic portion being non-stressed when the first and second elongated edge members are pivotally positioned centrally away from each other about the spinal longitudinal axis, so as to form a predetermined maximal spanning angle between opposing the interconnecting members. Optionally, the predetermined maximal spanning angle is within a range of between about 60° and about 140°. Optionally, the at least one elastic portion exhibits an increase in stress when subjected to a moment of force that pivotally shifts the first and second elongated edge members towards each other about the spinal longitudinal axis. Optionally, the first and second edge members are configured to approach each other so as to form a spanning angle between opposing the interconnecting members being equal to or greater than about 60", when each first and second elongated edge member or/and each tissue support member exerts a total lateral pressing force upon a corresponding prostatic lateral lobe, the total lateral pressing force being a range of between about 100 grams and about 1,000 grams.

According to some embodiments of the invention, wherein the at least one tissue support member is configured as a curvilinear portion of the first or/and second elongated edge member protruding towards the spinal longitudinal axis.

According to some embodiments of the invention, wherein the at least one tissue support member is configured as a curvilinear portion of the first or/and second elongated edge member that protrudes laterally outwardly from an area encompassed by the first or/and second elongated edge member and the spine member.

According to some embodiments of the invention, the at least one tissue support member is configured as a rib or rib-type member extending from one of the interconnecting members. Optionally, the rib or rib-type member is curved or bent laterally outwardly from a perimeter of area encompassed by a corresponding the elongated edge member and the spine member.

According to some embodiments of the invention, the at least one tissue support member comprises a tissue contacting surface sized or/and shaped according to dimensions of the prostatic lateral lobe portion.

According to some embodiments of the invention, the left and right posterolateral interlobar grooves, by continuously exerting a radially directed pushing force thereupon, within a range of between about 100 grams and about 1,000 grams, so as to prevent or minimize axial or/and rotational movement of the anchored anterior interlobar groove, and, the left and right posterolateral interlobar grooves.

According to some embodiments of the invention, the implant is configured to anchor the anterior interlobar groove, and, the left and right posterolateral interlobar grooves, by continuously exerting a radially directed pushing force thereupon, so as to increase distance separating superior portions of the interlobar grooves and increase distance separating left and right inferior portions of the interlobar grooves, or/and to maintain a distance of at least 2 mm between the prostatic lateral lobes, by exerting lateral forces thereupon within a range of between about 100 grams and about 1,000 grams.

According to some embodiments of the invention, at least one of the first and second elongated edge members comprises a cranial-nose portion shaped and configured for resting against a ledge, imposed by a urinary bladder neck segment adjacent the prostatic urethra, so as to prevent cranial dislodgement of the implant into urinary bladder, when the spine member engages an anterior interlobar groove that extends between the prostatic lateral lobes, and when the first and second elongated edge members engage corresponding posterolateral interlobar grooves. Optionally, the cranial-nose portion is "L" shaped. According to some embodiments of the invention, at least one of the first and second elongated edge members comprises a caudal-nose portion shaped and configured for resting against a narrowing, imposed by external urethral sphincter adjacent to verumontanum of the prostatic urethra, so as to prevent caudal migration of the implant through external sphincter and into bulbar urethra, when the spine member engages an anterior interlobar groove that extends between the prostatic lateral lobes, and when the first and second elongated edge members engage corresponding posterolateral interlobar grooves. Optionally, the caudal-nose portion is "L" shaped.

According to an aspect of some embodiments of the present invention, there is provided a system for retracting or/and supporting periurethral tissue enclosing a prostatic urethra along a length of prostate lobes, the system comprising an implant comprising a plurality of elongated edge members interconnected in a form of a collapsible-expandable frame expandable to retract or/and support periurethral tissue by exerting pushing forces upon interlobar grooves located along the prostatic urethra, wherein a first one of the elongated edge members includes a first craniolateral corner and a first caudolateral corner, and a second one of the elongated edge members includes a second craniolateral corner opposing the first craniolateral corner and a second caudolateral corner opposing the first caudolateral corner.

According to some embodiments of the invention, the implant manipulator detachably connected to the implant first and second elongated edge members, and configured to manipulate and force the first and second caudolateral corners into close proximity with each other, configured for progressively or sequentially changing shape or form of the implant according to different progressive or sequential implant deployment configurations including at least one of: a fully collapsed delivery configuration, whereby the first and second craniolateral corners are in close proximity with each other, and, the first and second caudolateral corners are in dose proximity with each other; a partially collapsed positioning configuration, whereby the first and second craniolateral corners are distanced apart from each other, and, the first and second caudolateral corners are in dose proximity with each other; and an expanded deployed configuration, whereby the first and second craniolateral corners are distanced apart from each other, and, the first and second caudolateral corners are distanced apart from each other.

According to some embodiments of the invention, the implant manipulator, when connected to the implant, is configured for applying thereto at least one of rotational forces, pulling forces, and pushing forces.

According to some embodiments of the invention, the implant manipulator comprises a tubular member and a tether releasably intertwined through both of the implant first and second caudolateral corners, the implant manipulator is configured for continuously or/and selectively pulling the implant via an operator using the tether against a distal end of the tubular member.

According to some embodiments of the invention, the system further comprises an over sheath sized for covering a length of a cystoscope having a cystoscope lumen dimensioned to restrain the implant in the fully collapsed delivery configuration via at least encircling the implant first and second craniolateral corners.

According to some embodiments of the invention, the implant manipulator is configured for facilitating and effecting the progressively or sequentially changing shape or form of the implant according to the different progressive or sequential implant deployment configurations. Optionally, the implant manipulator is configured for manipulating and shifting the implant within the over-sheath between the fully collapsed delivery configuration and the partially collapsed positioning configuration, by pushing or pulling the implant relative to the over-sheath lumen until the implant first and second craniolateral corners are released from the implant manipulator over sheath.

According to some embodiments of the invention, the implant manipulator is configured for manipulating and shifting the implant between the partially collapsed delivery configuration and the expanded deployed configuration by detaching from the implant after release of the tether from the implant first and second caudolateral corners.

According to some embodiments of the invention, the partially collapsed positioning configuration includes the implant having a frustum or cone-like shape whose distal-most diameter thereof is greater than smallest cross-sectional dimension in a urinary bladder neck pining the prostatic urethra, and whose proximal-most diameter thereof is smaller than the smallest cross-sectional dimension in the urinary bladder neck.

According to some embodiments of the invention, the implant comprises: an elongated spine member having a spinal longitudinal axis; and a first elongated edge member and a second elongated edge member symmetrically opposing each other relative to the spinal longitudinal axis, and interconnected to the spine member via at least one interconnecting member.

Optionally, the spine member has a length being equal to or less than length of an anterior interlobar groove that extends between prostatic lateral lobes, or/and substantially less than length of each of the first and second elongated edge members. Optionally, the first elongated edge member is sized for positioning in a left posterolateral interlobar groove that extends between a left prostatic lateral lobe and a prostatic medial lobe, and the second elongated edge member is sized for positioning in a right posterolateral interlobar groove that extends between a right prostatic lateral lobe and the prostatic medial lobe. According to some embodiments of the invention, at least one of the implant first and second craniolateral corners are shaped and configured for resting against a ledge imposed by urinary bladder neck so as to prevent cranial dislodgement of the implant into urinary bladder, when the spine member engages an anterior interlobar groove that extends between prostatic lateral lobes, and when the first and second elongated edge members engage corresponding posterolateral interlobar grooves.

According to some embodiments of the invention, at least one of the implant first and second caudolateral corners are shaped and configured for resting against a narrowing imposed by external urethral sphincter adjacent verumontanum of the prostatic urethra, so as to prevent caudal shift of the implant, when the spine member engages an anterior interlobar groove that extends between prostatic lateral lobes, and when the first and second elongated edge members engage corresponding posterolateral interlobar grooves. Optionally, each of the implant first and second caudolateral corners has a shape or form of a proximally directed apex, the apex being formed by intersection of converging curved slopes of respective ones of the implant first and second caudolateral corners.

According to an aspect of some embodiments of the present invention, there is provided a method for retracting or/and supporting periurethral tissue enclosing a prostatic urethra along a length of prostate lobes, the method comprising providing an implant along a chosen length of the prostate lobes. Optionally, the method also includes exerting continuous radially directed pushing forces upon an anterior interlobar groove between the prostate lobes, and upon at least one of left and right posterolateral interlobar grooves between the prostate lobes, thereby anchoring the implant in-place. Optionally, the method also includes exerting lateral pressing forces upon one or more prostatic lateral lobes, thereby retracting or/and supporting the periurethral tissue.

According to an aspect of some embodiments of the present invention, there is provided a method for retracting or/and supporting periurethral tissue enclosing a prostatic urethra along a length of prostate lobes, the method comprising providing an implant in a fully collapsed delivery configuration, the implant comprises an independently actuatable distal retractor incorporating first and second craniolateral corners, and an independently actuatable proximal retractor incorporating first and second caudolateral corners, wherein the first and second craniolateral corners are in close proximity to each other, and, the first and second caudolateral corners are in close proximity to each other.

Optionally, the method also includes passing the implant in the fully collapsed delivery configuration, in a cranial direction in a subject's urethra, into the subjects urinary bladder. Optionally, the method also includes expanding the distal retractor within inner boundaries of the urinary bladder. Optionally, the method also includes positioning under vision the implant in the prostatic urethra along the length of the prostate lobes. Optionally, the method also includes expanding the proximal retractor so as to effect changing configuration of the implant from the fully collapsed delivery configuration into an expanded deployed configuration, wherein the first and second craniolateral corners are distanced apart from each other, and, the first and second caudolateral corners are distanced apart from each other.

According to some embodiments of the invention, the providing includes collapsing the implant from a non-stressed fully opened configuration to the fully collapsed delivery configuration.

According to some embodiments of the invention, the collapsing includes at least one of urging the first and second caudolateral corners into the close approximation therebetween, using an implant manipulator, so as to effect the implant into the partially collapsed positioning configuration; and drawing a compression sleeve over entire length of the implant the compression sleeve incorporates a lumen sized for effecting the implant from the partially collapsed positioning configuration into the fully collapsed delivery configuration.

According to some embodiments of the invention, the urging includes pulling a tether, releasably intertwined through both the first and second caudolateral corners, against a distal end of a tubular member forming the implant manipulator, According to some embodiments of the invention, the passing includes at least one of: loading the implant manipulator with the implant connected thereto into a lumen of a urologic cystoscope; and pushing the implant distally through the urethra with the urologic cystoscope.

Optionally, the method also includes sleeving an over-sheath over a longitudinal body of the urologic cystoscope; and extending the over-sheath throughout length of the urethra with a distal end thereof provided adjacent or inside the urinary bladder. Optionally, the positioning or the expanding the proximal retractor includes or is preceded by removing the urologic cystoscope.

According to some embodiments of the invention, expanding the distal retractor effects the implant into a partially collapsed positioning configuration, whereby the first and second craniolateral corners are distanced one with each other, and, the first and second caudolateral corners are kept in close approximation therebetween.

Optionally, expanding the distal retractor includes releasing the distal retractor from a restricting boundary until the distal retractor protrudes in a cranial direction from a distal end of the over-sheath inner lumen.

According to some embodiments of the invention, the distal implant comprises an elongated spine member extending along a spinal longitudinal axis, and a first and a second elongated edge members connected to the spine member via interconnecting members, and symmetrically opposing each other relative to the spinal longitudinal axis. Optionally, the spine member is sized for positioning in an anterior interlobar groove that extends between lateral prostate lobes in the prostatic urethra. Optionally, the first elongated edge member is sized for positioning in a left posterolateral interlobar groove that extends between a left lateral prostate lobe and a middle prostate lobe, and the second elongated edge member is sized for positioning in a right posterolateral interlobar groove that extends between a right lateral prostate lobe and a middle prostate lobe.

According to some embodiments of the invention, positioning includes: rotating the implant by applying torque forces, relative to the spinal longitudinal axis so as to align the spine member with the anterior interlobar groove, or/and to align the first elongated edge member with the left posterolateral interlobar groove, or/and to align the second elongated edge member with the right posterolateral interlobar groove; and visually verifying the alignment using cystoscopy.

According to some embodiments of the invention, positioning includes pulling the implant in a caudal direction to a position within the prostatic urethra or/and placing the first and second craniolateral corners against a narrowing imposed by internal urethral sphincter adjacent to urine-bladder neck. Optionally, positioning includes inserting the spine member in the anterior interlobar groove, or/and inserting the first elongated edge member in the left posterolateral interlobar groove, or/and inserting the second elongated edge member in the right posterolateral interlobar groove.

According to some embodiments of the invention, positioning results in the implant, being in the partially collapsed positioning configuration, expanding a distal region of the prostatic urethra, using the distal retractor, into a greater lumen size than an adjacent proximal region of the prosthetic urethra According to some embodiments of the invention, positioning further results in the distal retractor partially collapsing into conforming with anatomy of the distal region of the prostatic urethra According to some embodiments of the invention, the implant comprises at least one tissue support member sized and configured for supporting a portion of a lateral prostatic lobe following the positioning. Optionally, the method further includes:

leaving the implant to continuously exert radially directed pushing forces upon the anterior interlobar groove and at least one of the left and right posterolateral interlobar grooves, so as to prevent or minimize axial or/and rotational movement thereof, or/and to increase distance separating the superior interlobar grooves and to increase distance separating the left and right inferior-lateral interlobar grooves.

According to some embodiments of the invention, leaving the implant includes exerting lateral pressing forces upon each lateral prostate lobe, thereby retracting or/and supporting the periurethral tissue.

Optionally, the method comprises repeating at least one of expanding the distal retractor, positioning and expanding the proximal retractor until reaching a chosen result Optionally, repeating includes: re-collapsing the implant back into the fully collapsed delivery configuration; and passing the implant back into a urinary bladder.

According to some embodiments of the invention, the chosen result is verified under vision. Optionally, the chosen result includes anchoring different portions of the implant in at least two of anterior interlobar groove, left posterolateral interlobar groove, and right posterolateral interlobar groove of the prostatic urethra within the boundaries of the prostate lobes. Optionally, the chosen result includes lifting both lateral prostate lobes so as to enlarge minimal lumen size of the prostatic urethra to at least 1 mm along a continuous length thereof.

According to some embodiments of the invention, lifting includes shifting each the lateral prostate lobe, pivotally, relatively to the anterior interlobar groove.

There is provided, in accordance with an embodiment, a dilating device for the prostatic urethra, the device comprising: at least three, laterally connected longitudinal ridges, wherein each ridge is configured to longitudinally engage with a different substantially longitudinally groove of the prostatic urethra of a patient, and wherein the at least three laterally connected ridges are configured to laterally compress to enable insertion into the prostatic urethra in a compressed configuration, and wherein the at least three laterally connected ridges are configured to laterally expand to a normally-open configuration upon deployment within the prostatic urethra, to exert a radially outwards force that dilates the prostatic urethra.

In some embodiments, the at least three laterally connected ridges comprise two peripheral ridges that are each configured to engage with a different postero-lateral groove of the prostatic urethra, and a central ridge that is configured to engage with the anterior inter-lobar groove of the prostatic urethra.

In some embodiments, there is further provided one or more connectors that laterally connect each peripheral ridge to the central ridge.

In some embodiments, the one or more connectors laterally connect each peripheral ridge to the central ridge at a point on each ridge that lies between the distal and proximal ends of the peripheral and central ridges.

In some embodiments, the one or more connectors comprise two distal connectors that laterally connect a distal end of each peripheral ridge to a distal end of the central ridge, and two proximal connectors that laterally connect a proximal end of each peripheral ridge to a proximal end of the central ridge, thereby forming two closed forms joined at the central ridge.

In some embodiments, the two closed forms comprise lengthwise oriented ovoid 100 ps that together form a figure-eight shape in the normally-open configuration.

In some embodiments, the two closed forms form two substantially rectangular shapes that span two substantially non-parallel planes in the normally-open configuration.

In some embodiments, the two distal connectors are substantially S-shaped, and are configured to span a portion of a cylinder in the normally-open configuration, thereby dilating the prostatic urethra at the bladder neck.

In some embodiments, the two proximal connectors are substantially S-shaped, forming a butterfly shape by the device in the normally-open configuration.

In some embodiments, all the at least three laterally connected ridges and one or more connectors are configured to maintain intimate contact with the prostate urethra mucosa.

In some embodiments, there is further provided two or more distally positioned protrusions that are configured to impinge against the postero-lateral side of the bladder neck, thereby preventing a migration of the device into the urinary bladder.

In some embodiments, the at least three laterally connected ridges are composed of wire.

In some embodiments, the at least three laterally connected ridges are composed of cut foil.

In some embodiments, the at least three laterally connected ridges are composed of super-elastic alloy.

In some embodiments, the at least three laterally connected ridges are composed of super-elastic polymer.

In some embodiments, the super-elastic polymer is a biodegradable polymer.

In some embodiments, the device is configured to allow free passage of a liquid when deployed in the prostatic urethra.

In some embodiments, the shape of the device is configured to reside within the prostatic urethra.

In some embodiments, the at least three, laterally connected ridges are further configured to: laterally compress for fitting within a deployment lumen, laterally expand to a normally-open configuration upon extraction from the deployment lumen, and exert the outwards radial force upon deployment within the prostatic urethra.

In some embodiments, the deployment lumen is configured to be housed within a work channel of a cystoscope.

In some embodiments, the deployment lumen is further provided with a fluid delivery lumen and balloon that are configured to deliver a fluid to the bladder to allow deploying the device within the prostatic urethra via the bladder.

In some embodiments, the at least three, laterally connected ridges are provided with one or more proximally disposed protrusion that are configured to releasably connect the device to an alignment mechanism housed within the deployment lumen.

In some embodiments, the alignment mechanism comprises a releasable string that 100 ps through the protrusions and runs through an alignment lumen.

In some embodiments, the device is configured for alignment within the prostatic urethra via a torque that is transferred from the alignment mechanism.

There is provided, in accordance with an embodiment, a method for dilating a prostatic urethra, the method comprising: inserting a dilating device into the urethra of a patient; aligning the dilating device within the prostatic urethra; positioning the dilating device within the prostatic urethra of the patient; and deploying the dilating device within the prostatic urethra, thereby causing the dilating device to: expand to a normally-open configuration, engage with the grooves of the prostatic urethra, exert a radially outwards force on the prostatic urethra, and dilate the prostatic urethra.

In some embodiments, positioning comprises extracting the device from a deployment lumen and inserting the device into the urinary bladder of the patient.

In some embodiments, positioning comprises drawing the device from the bladder into the prostate urethra.

In some embodiments, aligning comprises transferring a torque applied to an alignment mechanism connected to the device.

In some embodiments, the torque is applied by rotating an alignment lumen that is connected to the device.

In some embodiments, aligning comprises positioning a central ridge of the device for engaging with the anterior inter-lobar groove of the prostatic urethra and positioning two peripheral ridges of the device to each engage with a different posterolateral groove of the prostatic urethra.

In some embodiments, the method further comprises causing the device to laterally compress and retreat within the deployment lumen if the alignment or position of the device is incorrect.

In some embodiments, the method further comprises causing the device to impinge against the postero-lateral side of the bladder neck, thereby preventing a migration of the device into the urinary bladder.

In some embodiments, the method further comprises disconnecting the device from a deployment lumen provided to deploy the device.

In some embodiments, the method further comprises applying a positioning balloon to secure the position of the deployed device.

There is provided, in accordance with an embodiment, a kit for dilating a prostatic urethra, the kit comprising: a deployment lumen; and a dilating device which comprises: at least three, laterally connected ridges, wherein each ridge is configured to vertically engage with a different substantially vertical groove of the prostatic urethra of a patient, and wherein the at least three laterally connected ridges are configured to laterally compress to enable insertion into the prostatic urethra, in a compressed configuration, through said deployment lumen, and wherein the at least three laterally connected ridges are configured to laterally expand to a normally-open configuration upon deployment from said deployment lumen into the prostatic urethra, to exert a radially outwards force that dilates the prostatic urethra, In some embodiments, the at least three, laterally connected ridges are provided with one or more proximally disposed protrusion that are configured to releasably connect the device to an alignment mechanism housed within the deployment lumen.

In some embodiments, the alignment mechanism comprises a releasable string that 100 ps through the protrusions and runs through an alignment lumen.

In some embodiments, the device is configured for alignment within the prostatic urethra via a torque that is transferred from the alignment mechanism.

In some embodiments, the deployment lumen is configured to be housed within a work channel of a cystoscope.

In some embodiments, the deployment lumen is further provided with a balloon that is configured to position the device within the within the prostatic urethra.

In some embodiments, the at least three laterally connected ridges comprise two peripheral ridges that are each configured to engage with a different postero-lateral groove of the prostatic urethra, and a central ridge that is configured to engage with the anterior inter-lobar groove of the prostatic urethra.

In some embodiments, the kit further comprises one or more connectors that laterally connect each peripheral ridge to the central ridge.

In some embodiments, the one or more connectors laterally connect each peripheral ridge to the central ridge at a point on each ridge that lies between the distal and proximal ends of the peripheral and central ridges.

In some embodiments, the one or more connectors comprise two distal connectors that laterally connect a distal end of each peripheral ridge to a distal end of the central ridge, and two proximal connectors that laterally connect a proximal end of each peripheral ridge to a proximal end of the central ridge, thereby forming two closed forms joined at the central ridge.

In some embodiments, the two closed forms comprise lengthwise oriented ovoid 100 ps that together form a figure-eight shape in the normally-open configuration.

In some embodiments, the two closed forms form two substantially rectangular shapes that span two substantially non-parallel planes in the normally-open configuration.

In some embodiments, the two distal connectors are substantially S-shaped, and are configured to span a portion of a cylinder in the normally-open configuration, thereby dilating the prostatic urethra at the bladder neck.

In some embodiments, the two proximal connectors are substantially S-shaped, forming a butterfly shape by the device in the normally-open configuration.

In some embodiments, all the at least three laterally connected ridges and one or more connectors are configured to maintain intimate contact with the prostate urethra mucosa.

In some embodiments, the kit further comprises two distally positioned protrusion that are configured to impinge against the postero-lateral side of the bladder neck, thereby preventing a migration of the device into the urinary bladder.

In some embodiments, the at least three laterally connected ridges are composed of wire.

In some embodiments, the at least three laterally connected ridges are composed of cut foil.

In some embodiments, the at least three laterally connected ridges are composed of super-elastic alloy.

In some embodiments, the at least three laterally connected ridges are composed of super-elastic polymer.

In some embodiments, the super-elastic polymer is a biodegradable polymer.

In some embodiments, the device is configured to allow free passage of a liquid when deployed in the prostatic urethra.

There is provided, in accordance with an embodiment, a dilating device for the prostatic urethra, the device comprising: at least two dilating means of the prostate urethra, wherein the dilating means are connected by ridges that are configured to fix the dilating means in place within the prostate urethra and prevent their movements or dislodgement and wherein the dilating means are configured to laterally expand to a normally-open configuration upon deployment within the prostatic urethra, to exert a lateral outwards force that dilates the prostatic urethra.

In some embodiments, the dilating means comprise arcs that exert lateral forces on the lateral lobes.

In some embodiments, the dilating means comprise rings.

In some embodiments, the shape of the device in a normally open configuration is configured to reside within a delimiting surface of a longitudinally oriented tube.

In some embodiments, the device is shaped to reside within the prostate urethra. In some embodiments, the dilating means and connecting ridges of the device are configured to maintain intimate contact with the prostate urethra mucosa.

In addition to the exemplary aspects and embodiments described above, further aspects and embodiments will become apparent by reference to the figures and by study of the following detailed description.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 A schematically illustrates a cross sectional side view of a typical human anatomical region encompassing the lower part of the bladder, the prostate, and the prostatic urethra, absent of benign prostate hyperplasia (BPH);

FIG. 1B schematically illustrates a cross sectional top view of a portion of the anatomical region shown in FIG. 1A (dashed line double arrow 1B-1B therein), highlighting exemplary relative positions, configurations, and sizes of a prostatic urethra in a normal open condition and selected prostatic lobes [dashed line circles];

FIG. 1C schematically illustrates a cross sectional top view of the same portion of the anatomical region shown in FIG. 1A, exhibiting benign prostate hyperplasia (BPH), highlighting exemplary relative positions, configurations, and sizes of the prostatic urethra in an abnormal compressed condition and selected prostatic lobes [dashed line circles];

FIG. 1D illustrates the anatomy of a caudal portion of the bladder the prostrate and the posterior urethra;

FIG. 2A schematically illustrates a side view of an exemplary embodiment of an implant for retracting or/and supporting periurethral tissue enclosing a prostatic urethra along a length of prostate lobes, highlighting some prostatic implant components, in accordance with some embodiments of the invention;

FIG. 2B schematically illustrates the exemplary implant shown in FIG. 2A, highlighting the implant distal retractor exhibiting a non-stressed configuration, and the implant proximal retractor exhibiting a stressed configuration, in accordance with some embodiments of the invention;

FIG. 2C schematically illustrates the exemplary implant shown in FIG. 2A, highlighting the implant distal and proximal retractors exhibiting a non-stressed configuration, in accordance with some embodiments of the invention;

FIG. 2D schematically illustrates a front view of the prostatic implant shown in FIG. 2A exhibiting a stressed configuration, in accordance with some embodiments of the invention;

FIG. 2E schematically illustrates a front view of the prostatic implant shown in FIG. 2C exhibiting a non-stressed configuration, in accordance with some embodiments of the invention;

FIG. 3A schematically illustrates the exemplary embodiment of the stressed prostatic implant shown in FIG. 2D immediately following insertion thereof into the (BPH exhibiting) anatomical region portion shown in FIG. 1C, highlighting exemplary (insertion stage) positioning and configuration of the stressed prostatic implant relative to the (compressed) prostatic urethra and prostatic lobes [dashed line circles];

FIG. 3B schematically illustrates the exemplary prostatic implant shown in FIG. 3A following release thereof inside the (BPH exhibiting) anatomical region portion shown in FIG. 1C, highlighting exemplary (release stage) positioning and configuration of the non-stressed prostatic implant relative to the (compressed) prostatic urethra and prostatic lobes [dashed line circles];

FIG. 4A-4C schematically illustrate perspective, front, and top views, respectively, of another exemplary embodiment of an implant for retracting or/and supporting periurethral tissue enclosing a prostatic urethra along a length of prostate lobes, highlighting some prostatic implant components, in accordance with some embodiments of the invention;

FIG. 5 schematically illustrates the exemplary prostatic implant shown in FIG. 4C, highlighting inclusion therein of a plurality of exemplary tissue support members, each configured as a rib or rib-type member, in accordance with some embodiments of the invention;

FIG. 6 schematically illustrates the exemplary prostatic implant shown in FIG. 4C, highlighting inclusion therein of a pair of exemplary tissue support members with each member including a tissue contacting surface, in accordance with some embodiments of the invention;

FIG. 7A schematically illustrates an exemplary embodiment of a system for retracting or/and supporting periurethral tissue enclosing a prostatic urethra along a length of prostate lobes, highlighting some system components, wherein an exemplary prostatic implant (such as that shown in FIGS. 4A and 4C), in a stressed configuration and operatively connected to an exemplary cystoscope, is entirely held within an exemplary compression sleeve by an implant manipulator, in accordance with some embodiments of the invention;

FIGS. 7B-7C schematically illustrate exemplary embodiments of the system shown in FIG. 7A, highlighting progressive (sequential) stages of operation thereof, wherein the exemplary prostatic implant is deployed via progressively (sequentially) being pushed out of the compression sleeve by the implant manipulator, in accordance with some embodiments of the invention;

FIG. 7D schematically illustrates the exemplary prostatic implant shown in FIGS. 7A-7C, following deployment by the system, in a 'stand-alone' non-stressed expanded configuration after exiting the compression sleeve and detachment from the implant manipulator, in accordance with some embodiments of the invention; and FIGS. 8A-8L schematically illustrate various stages of delivering and deploying an exemplary prostatic implant in accordance with an embodiment of the current invention;

FIGS. 9-10 schematically illustrate components and operation of an exemplary system (such as prostatic implant system 400 shown in FIGS. 7A-7C), including various stages of delivering and deploying an exemplary prostatic implant (such as prostatic implant 300 shown in FIGS. 4A, 4C, and 7D), for retracting or/and supporting periurethral tissue enclosing a prostatic urethra along a length of prostate lobes, in accordance with some embodiments of the invention.

FIG. 11A-B illustrates a dilating device for the prostatic urethra from a perspective view and a top view, respectively, in accordance with an embodiment;

Figure 12A:
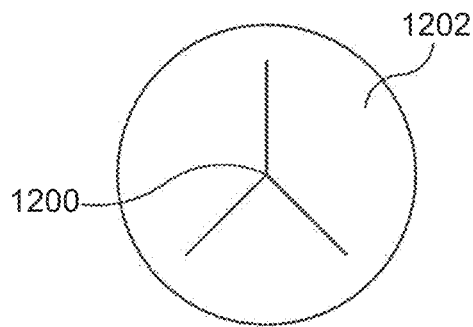
Figure 12B:
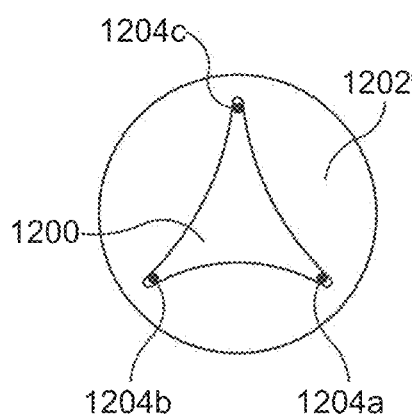
Figure 13A:
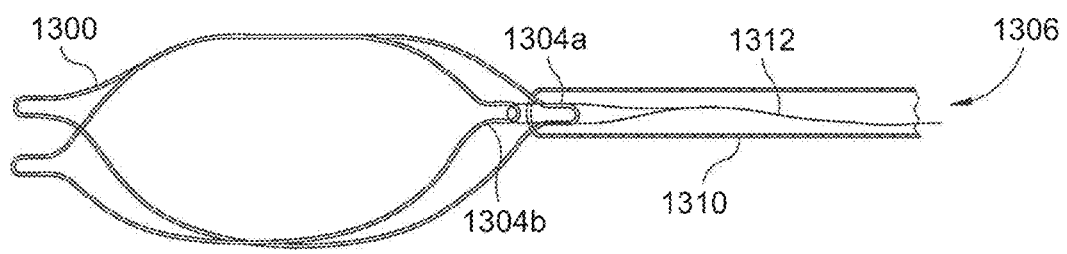
Figure 13B:
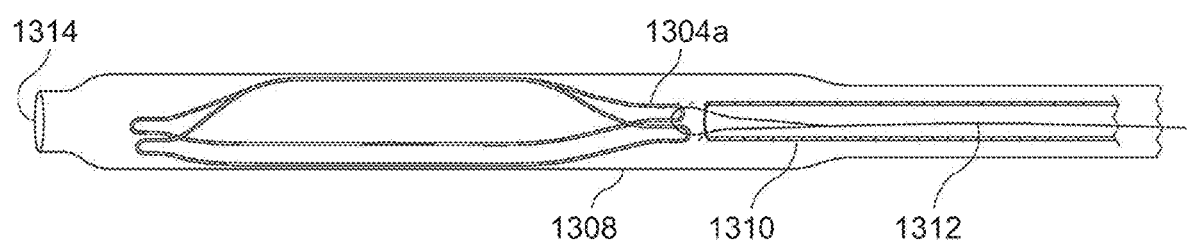
Figure 14A:
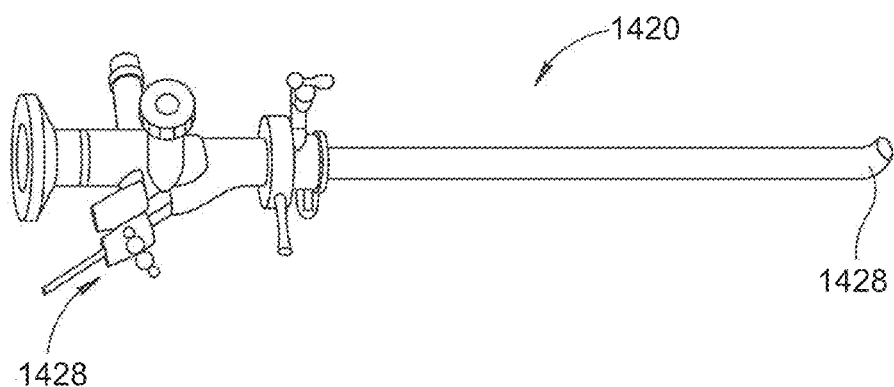
Figure 14B:
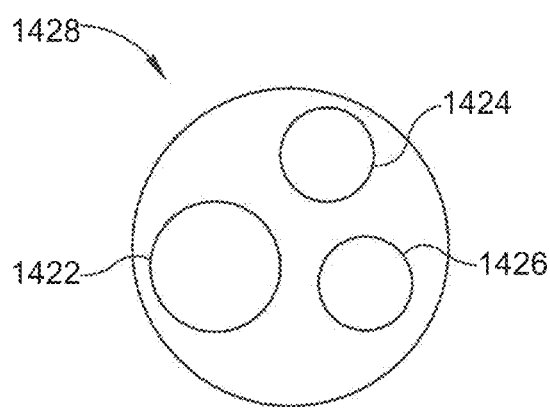
Figure 16:
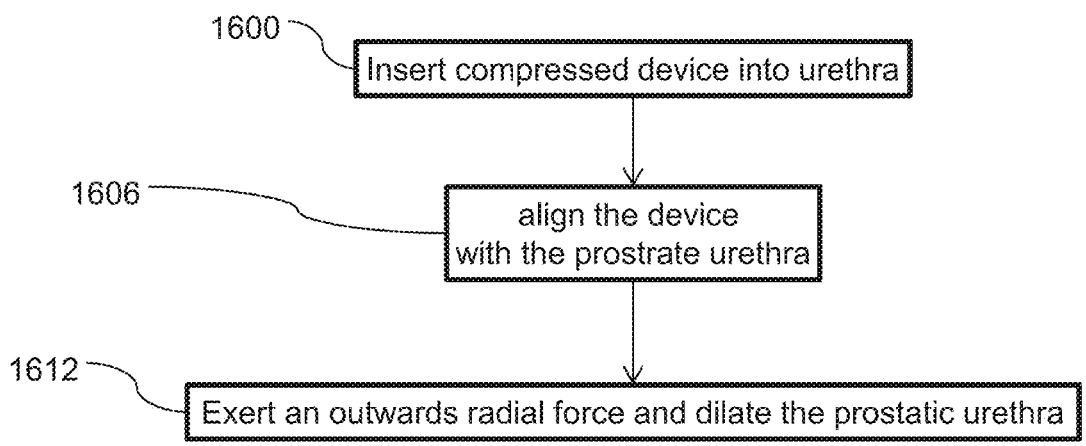
Figure 17:
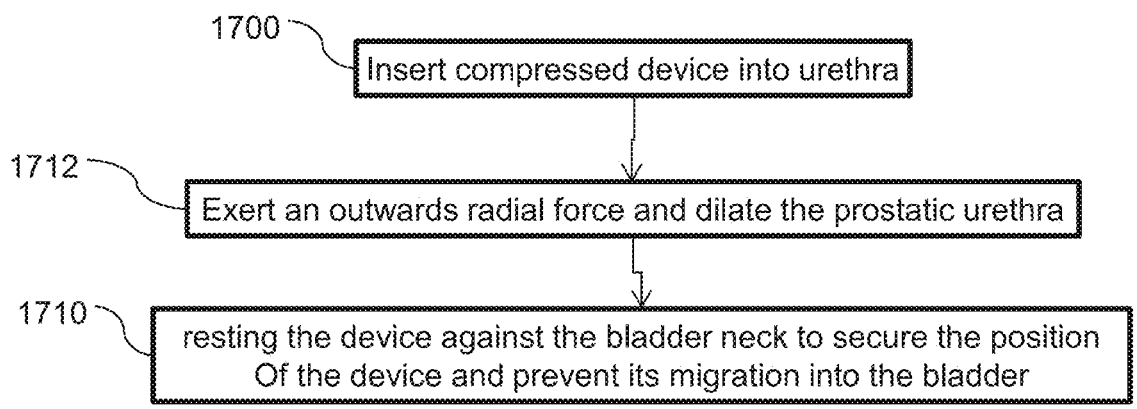
Figure 18:
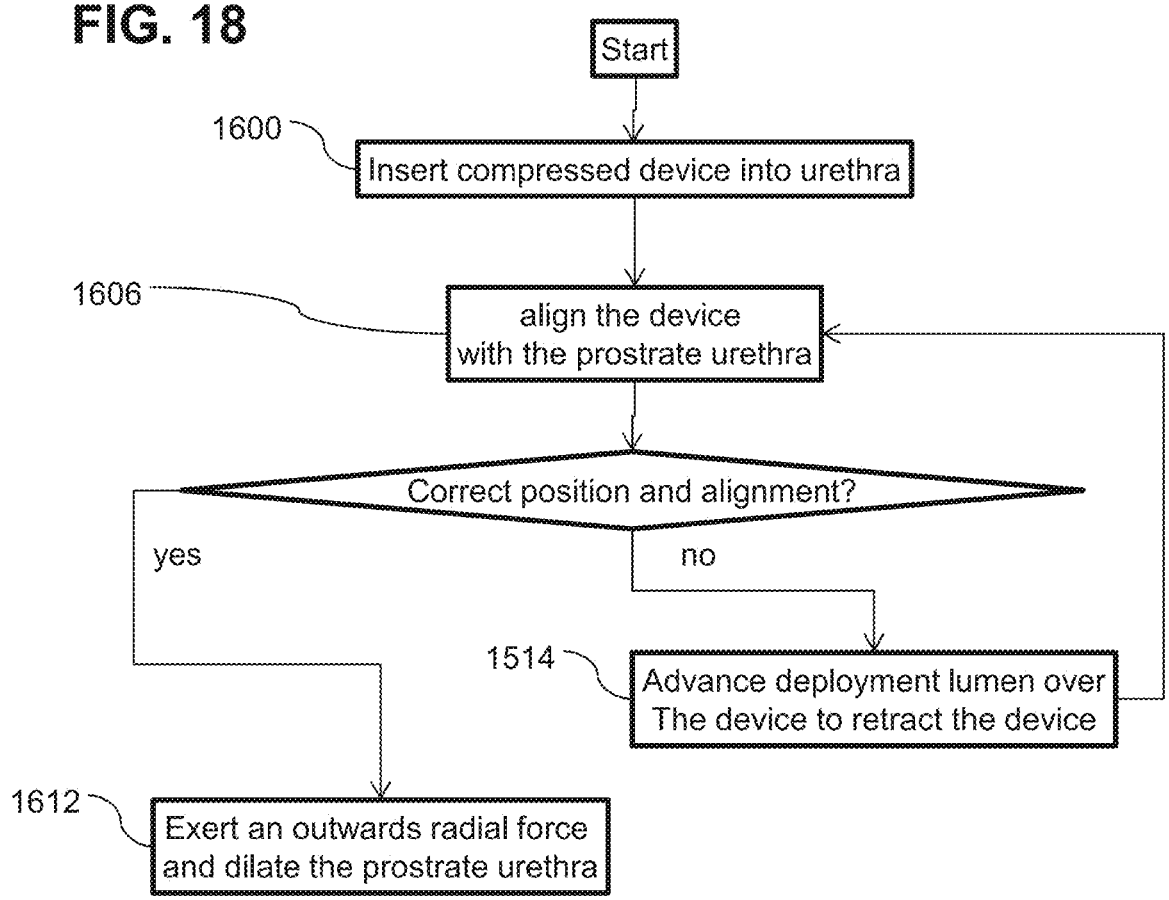
Figure 19:
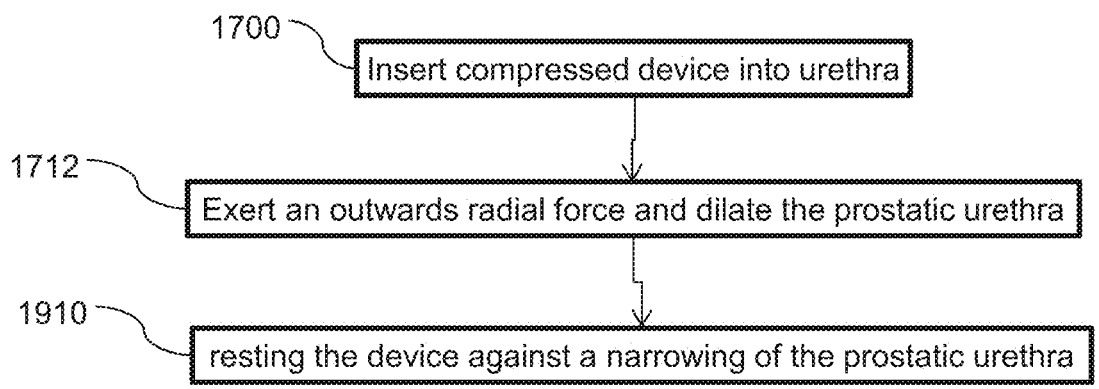

FIGS. 12A-B, together show an exemplary deployment of a device for dilating a prostatic urethra, according to an embodiment;

FIGS. 13A-B together illustrate a deployment apparatus for a dilating device for the prostatic urethra, in accordance with an embodiment;

FIGS. 14A-B show a cystoscope configured to deploy a dilating device for the prostatic urethra, in accordance with an embodiment;

FIG. 15 shows a flowchart of a method for dilating the prostatic urethra, according to an embodiment;

FIG. 16 shows a flowchart of a method for dilating the prostatic urethra, according to an embodiment;

FIG. 17 shows a flowchart of a method for inhibiting migration of a device in the prostatic urethra, according to an embodiment;

FIG. 18 shows a flowchart of a method for aligning a device in the prostatic urethra, according to an embodiment;

FIG. 19 shows a flowchart of a method for inhibiting migration of a device in the prostatic urethra, according to an embodiment.

DESCRIPTION OF SPECIFIC EMBODIMENTS
OF THE INVENTION

The present invention, in some embodiments thereof, relates to the field of urological medical devices and applications thereof, and more particularly, but not exclusively, to a urological (prostatic) implant, system, and method for retracting or/and supporting periurethral tissue enclosing a prostatic urethra along a length of prostate lobes, Disclosed herein is a device that is configured to dilate the prostatic urethra by engaging with the three grooves of the prostatic urethra and exerting a radially outwards force upon deployment within the urethra. The device may be normally open, and made of a resilient material allowing it to laterally compress for fitting within a deployment lumen, and to laterally expand to a normally-open configuration upon extraction from the deployment lumen, and exert the outwards radial force that dilates the prostatic urethra upon deployment.

For purposes of better understanding some embodiments of the present invention, as illustrated in FIGS. 2 TO 19, reference is first made to the anatomy of a caudal portion of the bladder 102 the prostrate 104 and the posterior urethra as illustrated in FIGS. 1A to 1D. As illustrated in FIGS. 1A to 1D, the posterior urethra includes three segments the pre-prostatic urethra 105, the prostatic urethra 106 and the membranous urethra 107.

The pre-prostatic urethra 105 (also called intra-mural) segment is this cranial most segment is located in the bladder neck 108 and surrounded by a smooth sphincter.

The prostatic urethra 106 (intra pelvic) segment begins at the bladder neck 108 and goes through the prostate 104 over 2 to 3 cm, keeping an almost vertical direction.

The membranous urethra 107 is a short portion of 1 to 2 cm going through the pelvic floor obliquely forwards and downwards. It is surrounded by the external sphincter 662.

FIG. 1 A schematically illustrates a cross sectional side view of a typical human anatomical region 100 encompassing the lower part of the urinary bladder 102, the prostate 104, and the prostatic urethra 106, where the anatomical region is absent of benign prostate hyperplasia (BPH). The prostatic urethra 106 is surrounded by and extends through the prostate 104 towards the bladder neck 108 of the urinary bladder 102.

In the context of schematically illustrating and visualizing benign prostate hyperplasia (BPH), of particular interest are characteristics and parameters of, or relating to, position, configuration, and size (diameter) of the prostatic urethra 106 relative to those of the various prostatic lobes of the prostate 104 surrounding the prostatic urethra 106. FIG. 1B schematically illustrates a cross sectional top view of a portion 110 of the anatomical region 100 shown in FIG. 1A (indicated by the dashed line double arrow 1B-1B therein), highlighting exemplary relative positions, configurations, and sizes of a prostatic urethra 106 in a normal open condition and selected prostatic lobes [dashed line circles], namely, left and right prostatic lateral lobes 114a and 114b, respectively, and prostatic medial lobe 116, during 'normal' conditions absent of BPH.

FIG. 1C schematically illustrates a cross sectional top view of the same portion 110 of the anatomical region 100 shown in FIG. 1A, exhibiting benign prostate hyperplasia (BPH), highlighting exemplary relative positions, configurations, and sizes of the prostatic urethra 106 in an abnormal compressed condition and selected prostatic lobes [dashed line circles], namely, left and right prostatic lateral lobes 114a and 114b, respectively, and prostatic medial lobe 116, during 'abnormal' conditions due to BPH. For additional illustrative purposes, FIG. 1C also shows the anterior interlobar groove 118, and, the left and right posterolateral interlobar grooves 120a and 120b, respectively, so formed as a result of 'abnormal' enlargement of prostatic lobes 114a, 114b, and 116, along with 'abnormal' compression of prostatic urethra 106.

As illustrated in FIG. 1A, the prostatic urethra 106 runs through the prostate 104 eccentrically, with most of the prostatic tissue posterior thereto. The posterior wall of the prostatic urethra contains the urethral crest 662, which is bordered laterally by posteriolateral grooves 664 (prostatic sinuses), into which the prostatic glands drain. The most prominent aspect of this crest is the seminal colliculus, or verumontanum, where the paired ejaculatory ducts 666 and the opening of the prostatic utricle 668 (a small midline paramesonephric duct remnant) meet the lumen of the urethra.

In the context of the relevant medical fields relating to, and associated with, the present invention, for the purpose of further enhancing understanding of the illustrative description of the numerous exemplary embodiments of the invention, herein following are meanings of structural and anatomical reference directions used in the hereinbelow illustrative description. The following meanings are presented in a non-limiting manner, whereby, other similar meanings may also be applicable to exemplary embodiments of the herein disclosed invention.

The term 'distal' (direction), as used herein, refers to the direction away from a medical practitioner performing a method or using a device, and closer to a subject's body or towards the midline of the subject's body. The term 'proximal' (direction), as used herein, refers to the direction towards the medical practitioner performing a method or using a device, and farther from a subjects body or away from the midline of the subjects body.

The term 'cranial' (direction), as used herein, refers to the direction generally towards a subject's head or brain, or, for example, in a direction towards a urinary bladder and away from a prostate of same subject. The term 'caudal' (direction), as used herein, refers to the direction opposite that of a subjects head or brain, or/and situated in or directed toward the part of the subject's body from which the tail arises.

The term 'anterior* (direction), as used herein, refers to the direction towards the front plane of a subject's body. The term posterior' (direction), as used herein, refers to the direction towards the rear plane of a subject's body.

The term 'lateral' (direction), as used herein, refers to the direction away from the median and sagittal plane of a subject's body. The term 'medial' (direction), as used herein, refers to the direction towards the median and sagittal plane of a subject's body.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

An aspect of some embodiments of the present invention is an implant (herein, also referred to as a prostatic implant) for retracting or/and supporting periurethral tissue enclosing a prostatic urethra along a length of prostate lobes. FIG. 2A schematically illustrates a side view of an exemplary embodiment of an implant (indicated as, and referred to by, reference number 200) for retracting or/and supporting periurethral tissue enclosing a prostatic urethra along a length of prostate lobes, highlighting some prostatic implant components. Exemplary prostatic implant 200, in a non-limiting manner, includes: a distal retractor 202 incorporating a first craniolateral corner 204a and a second craniolateral corner 204b, and a proximal retractor 206 incorporating a first caudolateral corner 208a and a second caudolateral corner 208b.

In exemplary embodiments, the prostatic implant 200 additionally includes an elongated spine member 210. In such exemplary embodiments, the distal retractor 202 is connected to, or integrally formed as a single structure with, the proximal retractor 206, via the elongated spine member 210 extending along a spinal longitudinal axis 212 or/and a plurality of elongated edge members 214 and 216.

In exemplary embodiments, the distal retractor 202 and the proximal retractor 206 are independently actuatable. Specifically, actuation (i.e., movement or/and change in configuration, shape or form, or/and position) of the distal retractor 202 is independent of actuation (movement or/and change in configuration, shape or form, or/and position) of the proximal retractor 206, and vice versa. Such independent actuation of the distal retractor 202 and the proximal retractor 206 is exemplified in FIGS. 2B and 2C. FIG. 2B schematically illustrates the exemplary prostatic implant 200 shown in FIG. 2A, highlighting the implant distal retractor 202 exhibiting a non-stressed configuration, and the implant proximal retractor 206 exhibiting a stressed configuration. FIG. 2C schematically illustrates the exemplary prostatic implant 200, highlighting both the implant distal retractor 202 and the proximal retractor 206 exhibiting a non-stressed configuration.

Accordingly, exemplary prostatic implant 200 is capable of undergoing a structural change in a manner whereby, for example, the distal retractor 202 is not actuated and remains in a non-stressed configuration (as shown in both FIGS. 2B and 2C), whereas the proximal retractor 206 is actuated and changes or shifts from a stressed configuration (FIG. 2B) to a non-stressed configuration (FIG. 2C). Such actuation, in the form of configurational change or shift, of the proximal retractor 206 is independent of non-actuation of the distal retractor 202.

An additional example showing preceding illustratively described structural change of the exemplary prostatic implant 200 is provided in FIGS. 2D-2E. FIG. 2D schematically illustrates a front view of the prostatic implant 200 shown in FIG. 2A exhibiting a stressed configuration, while FIG. 2E schematically illustrates a front view of the prostatic implant 200 shown in FIG. 2C exhibiting a non-stressed configuration. Such structural change of the exemplary prostatic implant 200 (in changing from a stressed configuration of FIG. 2D to a non-stressed configuration of FIG. 2E) is accompanied by radially directed forces outwardly originating from the distal and proximal retractors 202 and 206, respectively, in a manner such that the prostatic implant 200 laterally expands and changes from a stressed configuration (FIG. 2D) to a non-stressed configuration (FIG. 2E).

Exemplary implementation and use of a prostatic implant, for example, prostatic implant 200, for retracting or/and supporting periurethral tissue enclosing a prostatic urethra along a length of prostate lobes, according to some embodiments of the invention, are illustratively described with reference to FIGS. 3A and 3B.

Figure 1D:
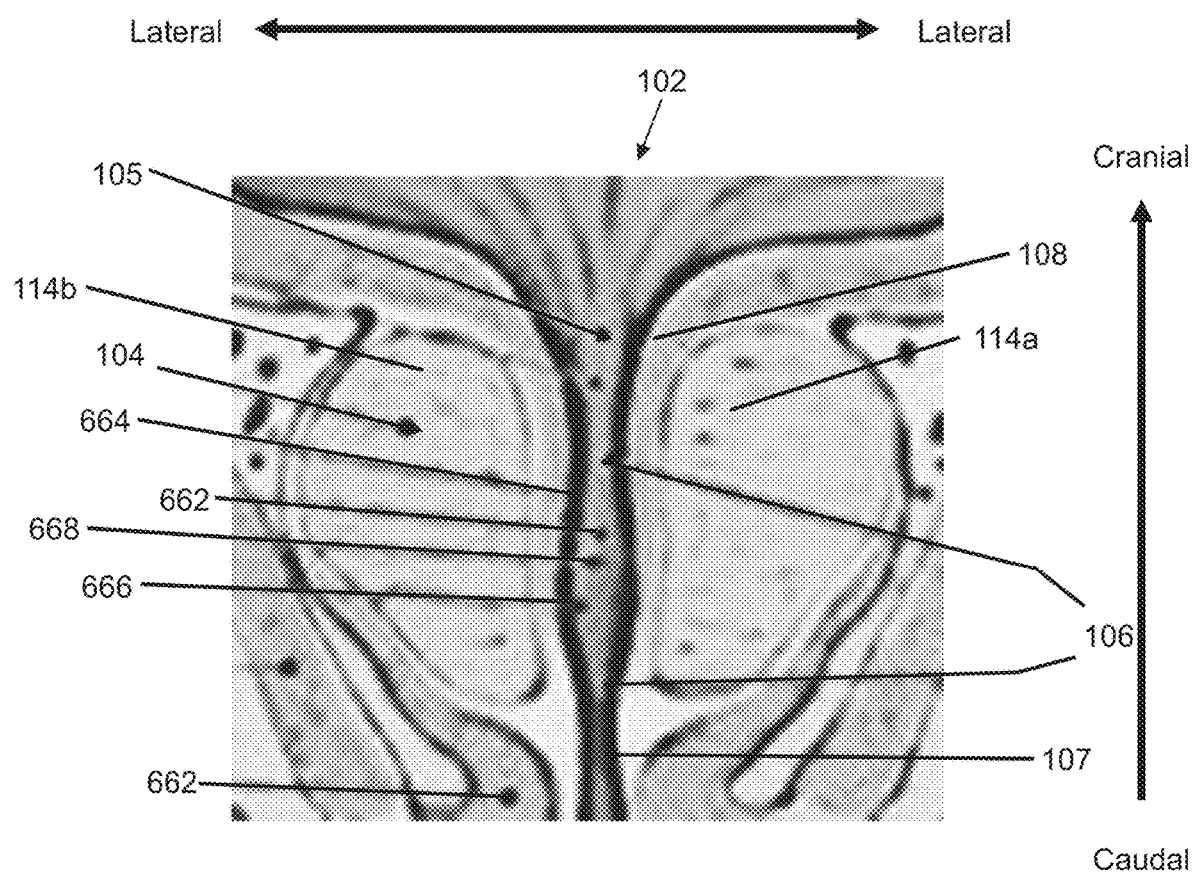
Figure 3A:
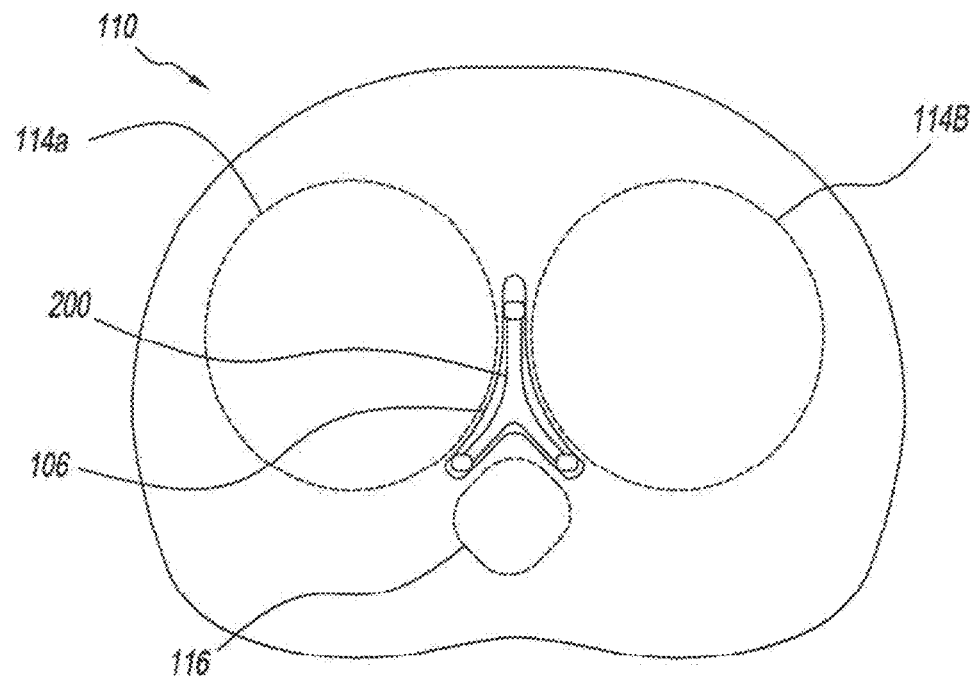

FIG. 3A schematically illustrates the exemplary embodiment of the stressed prostatic implant 200 shown in FIG. 2D immediately following insertion thereof into the (BPH exhibiting) anatomical region portion 110 shown in FIG. 1C. FIG. 3A highlights exemplary (insertion stage) positioning and configuration of the stressed prostatic implant 200 relative to the compressed prostatic urethra 106 and the prostatic lobes (left and right prostatic lateral lobes 114a and 114b, respectively, and prostatic medial lobe 116).

Figure 3B:
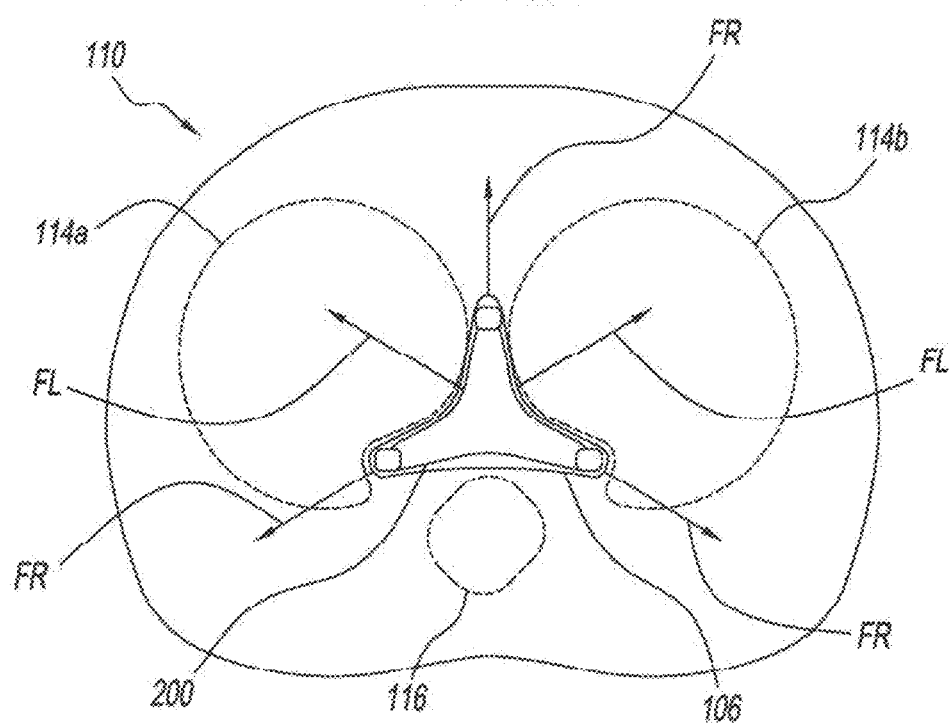

FIG. 3B schematically illustrates the exemplary prostatic implant 200 shown in FIG. 3A following release thereof inside the (BPH exhibiting) anatomical region portion 110. FIG. 3B highlights exemplary (release stage) positioning and configuration of the prostatic implant 200 now being less-stressed' (e.g., by undergoing elastic deformation under smaller external stresses, resulting in less strain thereof) relative to the compressed prostatic urethra 106 and the prostatic lobes. Structural change of the prostatic implant 200 (in changing from a stressed configuration of FIG. 3A to a non-stressed configuration of FIG. 3B) is accompanied by radially directed forces FR outwardly originating from the distal and proximal retractors 202 and 206, respectively, in a manner such that the prostatic implant 200 laterally expands and changes from a stressed configuration (FIG. 3A) to a partially- or less-stressed configuration (FIG. 3B). This, at least effects anchoring of implant 200 within the particular anatomy of the BPH prostatic urethra, which prevents dislodgement or migration thereof in cranial or caudal directions, as well as rotational movement Moreover, such structural change of the prostatic implant 200, via the radially directed forces FR outwardly originating from the distal and proximal retractors 202 and 206, respectively, translates into laterally directed pushing or pressure forces FL exerted by the distal and proximal retractors 202 and 206, respectively, upon those portions of the prostatic lobes (left and right prostatic lateral lobes 114a and 114b, respectively, and prostatic medial lobe 116) in contact with the prostatic implant 200, in general, and in contact with the distal and proximal retractors 202 and 206, respectively, in particular.

Additional exemplary and optional technical features, characteristics, and properties of an implant, for example, prostatic implant 200, for retracting or/and supporting periurethral tissue enclosing a prostatic urethra along a length of prostate lobes, according to some embodiments of the invention, are illustratively described as follows.

In exemplary embodiments, the distal retractor 202 or/and the proximal retractor 206 are in a form of a pair of first and second curved wing-like structures connected to spine member 210 via interconnecting members 217, and symmetrically opposing each other relative to the spinal longitudinal axis 212. In exemplary embodiments, each interconnecting member includes at least one elastic portion, for example, elastic portion 218, adjoining the spine member 210, such that the elastic portion is non-stressed when the first curved wing-like structure in the pair is pivotally positioned centrally away from the second curved wing-like structure in the pair about the spinal longitudinal axis 212, so as to form a predetermined maximal elongated edge member spanning angle. In exemplary embodiments, each elastic portion adjoining the spine member 210 exhibits an increase in stress (e.g., bending or/and compression) when subjected to a moment of force that pivotally shifts the first curved wing-like structure towards the second curved wing-like structure about the spinal longitudinal axis 212.

In exemplary embodiments, the prostatic implant 200 additionally includes at least one tissue support member extending between a first elongated edge member, for example, first elongated edge member 214, and the spinal longitudinal axis 212, and at least one other tissue support member extending between a second elongated edge member, for example, second elongated edge member 216, and the spinal longitudinal axis 212. In exemplary embodiments, each tissue support member is sized and configured for supporting a portion of a prostatic lateral lobe, for example, left prostatic lateral lobe 114a or right prostatic lateral lobe 114b, when the spine member 210 engages an anterior interlobar groove, for example, anterior interlobar groove 118, that extends between left and right prostatic lateral lobes 114a and 114b, respectively, and when the first and second elongated edge members 214 and 216, respectively, engage corresponding posterolateral interlobar grooves, for example, left and right posterolateral interlobar grooves 120a and 120b, respectively. In exemplary embodiments, the spine member 210 has a length being equal to or less than length of the anterior interlobar groove 118 or/and substantially less than the length of each of the first and second elongated edge members 214 and 216, respectively. In exemplary embodiments, the first elongated edge member 214 is sized for positioning in the left posterolateral interlobar groove 120a that extends between the left prostatic lateral lobe 114a and the prostatic medial lobe 116, and the second elongated edge member 216 is sized for positioning in the right posterolateral interlobar groove 120b that extends between the right prostatic lateral lobe 114b and the prostatic medial lobe 116.

FIGS. 4A-4C schematically illustrate a perspective view, a frontal view, and a top view, respectively, of another exemplary embodiment of an implant (indicated as, and referred to by, reference number 300) for retracting or/and supporting periurethral tissue enclosing a prostatic urethra along a length of prostate lobes, highlighting some prostatic implant components. According to such an exemplary embodiment, exemplary prostatic implant 300, in a non-limiting manner, includes: a distal retractor 302 incorporating a first craniolateral corner 304a and a second craniolateral corner 304b, and a proximal retractor 306 incorporating a first caudolateral corner 308a and a second caudolateral corner 308b.

In exemplary embodiments, the prostatic implant 300 additionally includes an elongated spine member 310. In such exemplary embodiments, the distal retractor 302 is connected to, or integrally formed as a single structure with, the proximal retractor 306, via the elongated spine member 310 extending along a spinal longitudinal axis 312 or/and a plurality of elongated edge members, for example, first and second elongated edge members, 314 and 316, respectively.

In exemplary embodiments, the distal retractor 302 and the proximal retractor 306 are independently actuatable. Specifically, actuation (i.e. movement or/and change in configuration, shape or form, or/and position) of the distal retractor 302 is at least partly, or entirely, independent of actuation (movement or/and change in configuration, shape or form, or/and position) of the proximal retractor 306, and vice versa. In exemplary embodiments, such actuation may be in the form of an 'indirect actuation', for example, by indirectly actuating the distal retractor 302 or/and the proximal retractor 306 using external means. In such exemplary embodiments, the indirect external means may include or involve using an implant delivery system, for example, in a form of an operative combination of an implant manipulator and a compression sleeve, for example, implant manipulator 410 and compression sleeve 404 illustratively described hereinbelow and shown in FIGS. 7A-7C, and 8A—8L, in the context of an exemplary embodiment of a prostatic implant system).

Independent actuation of the distal retractor 302 and the proximal retractor 306 of prostatic implant 300 is analogous to that exemplified for the distal retractor 202 and the proximal retractor 206 of prostatic implant 200 shown in FIGS. 2B and 2C. Thus, similar to that shown in FIG. 2B, for the exemplary prostatic implant 300 shown in FIGS. 4A-4C, the implant distal retractor 302 may exhibit a non-stressed configuration, while the implant proximal retractor 306 may exhibit a stressed configuration. Additionally, similar to that shown in FIG. 2C, for the exemplary prostatic implant 300, both the implant distal retractor 302 and the proximal retractor 306 may exhibit a non-stressed configuration.

Accordingly, exemplary prostatic implant 300 is capable of undergoing a structural change in a manner whereby, for example, the distal retractor 302 is not actuated and remains in a non-stressed configuration (analogous to that shown in both FIGS. 2B and 2C), whereas the proximal retractor 306 is actuated and changes or shifts from a stressed configuration (analogous to that shown in FIG. 2B) to a non-stressed configuration (analogous to that shown in FIG. 2C). Such actuation, in the form of configurational change or shift, of the proximal retractor 306 is independent of non-actuation of the distal retractor 302.

Preceding illustratively described structural change of the exemplary prostatic implant 300 shown in FIGS. 4A-4C is analogous to that illustratively described hereinabove regarding structural change of the exemplary prostatic implant 200 as shown in FIGS. 2D-2E. Accordingly, such structural change of the exemplary prostatic implant 300 in changing from a stressed (e.g., compressed) configuration (analogous to that shown in FIG. 2D) to a non-stressed (e.g., non-compressed) configuration (analogous to that shown in FIG. 2E), is accompanied by radially directed forces outwardly originating from the distal and proximal retractors 302 and 306, respectively, in a manner such that the prostatic implant 300 laterally expands and changes from a stressed configuration to a non-stressed configuration.

Exemplary implementation and use of the prostatic implant 300, for retracting or/and supporting periurethral tissue enclosing a prostatic urethra along a length of prostate lobes, according to some embodiments of the invention, are analogous to that illustratively described hereinabove regarding the exemplary prostatic implant 200 as shown in FIGS. 3A and 3B.

Accordingly, in a manner analogous to that shown in FIG. 3A, prostatic implant 300, when in a stressed (e.g., compressed or folded) configuration, may be inserted 1700 (for example see FIG. 17) into the (BPH exhibiting) anatomical region portion 110 shown in FIG. 1C. For example, with reference made to FIG. 3A, exemplary prostatic implant 200 can be substituted with exemplary prostatic implant 300, for highlighting exemplary (insertion stage) positioning and configuration of the stressed (compressed or folded) prostatic implant 300 relative to the (compressed) prostatic urethra 106 and the prostatic lobes (left and right prostatic lateral lobes 114a and 114b, respectively, and prostatic medial lobe 116).

Additionally, for example, with reference made to FIG. 3B, exemplary prostatic implant 200 can be substituted with exemplary prostatic implant 300, for schematically illustrating the stressed (compressed or folded) configuration of exemplary prostatic implant 300 following release thereof inside the (BPH exhibiting) anatomical region portion 110. According to such analogy, FIG. 3B, prostatic implant 200 being replaced by prostatic implant 300, would then highlight exemplary (release or unfolding stage) positioning and configuration of the less-stressed' (partially or entirely unfolded) prostatic implant 300 relative to the 'more-stressed' prostatic urethra 106 and the prostatic lobes. Structural change of the prostatic implant 300 (in changing from the stressed (compressed or folded) configuration to the non-stressed (partially or entirely unfolded) configuration is accompanied by radially directed forces outwardly originating from the distal and proximal retractors 302 and 306, respectively, in a manner such that the prostatic implant 300 laterally expands (i.e., unfolds) and changes from a stressed (compressed or folded) configuration to a non-stressed (partially or entirely unfolded) configuration. Moreover, such structural change of the prostatic implant 300, via the radially directed forces outwardly originating from the distal and proximal retractors 302 and 306, respectively, translates into laterally directed pushing or pressure forces exerted 1712 by the distal and proximal retractors 302 and 306, respectively, upon those portions of the prostatic lobes (left and right prostatic lateral lobes 114a and 114b, respectively, and prostatic medial lobe 116) in contact with the prostatic implant in general, and in contact with the distal and proximal retractors 302 and 306, respectively, in particular.

Reference is again made to FIG. 4A, schematically illustrating a perspective view of exemplary prostatic implant 300, for retracting or/and supporting periurethral tissue enclosing a prostatic urethra along a length of prostate lobes, highlighting some prostatic implant components. According to such an alternative exemplary embodiment exemplary prostatic implant 300, in a non-limiting manner, includes: an elongated spine member 310 having a spinal longitudinal axis 312, and, a first elongated edge member 314 and a second elongated edge member 316 symmetrically opposing each other relative to the spinal longitudinal axis 312. Therein, each of the first and second elongated edge members 314 and 316, respectively, is interconnected to the spine member 310 via at least one interconnecting member, for example, interconnecting member 320.

According to this exemplary embodiment exemplary prostatic implant 300 additionally includes at least one tissue support member, for example, first tissue support member 322, extending between the first elongated edge member 314 and the spinal longitudinal axis 312, and at least one other tissue support member, for example, second tissue support member 324, extending between the second elongated edge member 316 and the spinal longitudinal axis 312. Therein, each of the tissue support members, for example, each of the first and second tissue support members 322 and 324, respectively, is sized and configured for supporting a portion of a prostatic lateral lobe (for example, left or right prostatic lateral lobe 114a or 114b, respectively, shown in FIGS. 1C, 3A, 3B) when the spine member 310 engages an anterior interlobar groove (for example, anterior interlobar groove 118 shown in FIGS. 1C, 3A, 3B) that extends between prostatic lateral lobes, and when the first and second elongated edge members 314 and 316, respectively, engage corresponding posterolateral interlobar grooves (for example, left and right posterolateral interlobar grooves 120a and 120b, shown in FIGS. 1C, 3A, 3B).

Additional exemplary and optional technical features, characteristics, and properties of an implant, for example, prostatic implant 300, for retracting or/and supporting periurethral tissue enclosing a prostatic urethra along a length of prostate lobes, according to some embodiments of the invention, are illustratively described as follows.

In exemplary embodiments, the spine member 310 has a length being equal to or less than length of the anterior interlobar groove 118 or/and substantially less than the length of each of the first and second elongated edge members 314 and 316, respectively. In exemplary embodiments, the first elongated edge member 314 is sized for positioning in the left posterolateral interlobar groove 120a that extends between the left prostatic lateral lobe 114a and the prostatic medial lobe 116, and the second elongated edge member 316 is sized for positioning in the right posterolateral interlobar groove 120b that extends between the right prostatic lateral lobe 114b and the prostatic medial lobe 116.

In exemplary embodiments, the prostatic implant 300 is configured to anchor the anterior interlobar groove 118, and, the left and right posterolateral interlobar grooves 120a and 120b, respectively, by continuously exerting a radially directed pushing force thereupon, within a range of between about 100 grams and about 1,000 grams, so as to prevent or minimize axial or/and rotational movement of the anchored anterior interlobar groove 118, and, the posterolateral interlobar grooves 120a and 120b. In exemplary embodiments, the prostatic implant 300 is configured to anchor the anterior interlobar groove 118, and, the left and right posterolateral interlobar grooves 120a and 120b, respectively, by continuously exerting a radially directed pushing force thereupon, so as to increase distance separating superior portions of the interlobar grooves and increase distance separating left and right inferior portions of the interlobar grooves, or/and to maintain a distance of at least 2 mm between the prostatic lateral lobes, by exerting lateral forces thereupon within a range of between about 100 grams and about 1,000 grams.

In exemplary embodiments, implant 300 is shown in FIG. 4A as fully unfolded and fully unstressed, having its double wings-like structure fully opened and expanded laterally. In exemplary embodiments, each of the interconnecting members, for example, interconnecting member 320, includes at least one elastic portion, for example, elastic portion 328, adjoining the spine member 310, such that the elastic portion 328 is non-stressed when the first and second elongated edge members 314 and 316, respectively, are pivotally positioned centrally away from each other about the spinal longitudinal axis 312, so as to form a predetermined maximal spanning angle between opposing interconnecting members. In exemplary embodiments, the predetermined maximal spanning angle is within a range of between about 60 degrees and about 140 degrees. In exemplary embodiments, each elastic portion, for example, elastic portion 328, adjoining the spine member 310 exhibits an increase in stress (compression) when subjected to a moment of force that pivotally shifts the first and second elongated edge members 314 and 316, respectively, towards each other about the spinal longitudinal axis 312.

In exemplary embodiments, the first and second edge members 314 and 316, respectively, are configured to approach each other so as to form an elongated edge member spanning angle being equal to or greater than about 60° degrees. In such exemplary embodiments, each of the first and second elongated edge members 314 and 316, respectively, or/and each of the first and second tissue support members 322 and 324, respectively, exerts a total lateral pressing force upon a corresponding prostatic lateral lobe. In exemplary embodiments, the total lateral pressing force is in a range of between about 100 grams and about 1,000 grams.

In exemplary embodiments, each of the first and second tissue support members 322 and 324, respectively, is configured as a curvilinear portion of the first elongated edge member 314 or/and the second elongated edge member 316 protruding towards the spinal longitudinal axis 312. In exemplary embodiments, each of the first and second tissue support members 322 and 324, respectively, is configured as a curvilinear portion of the first elongated edge member 314 or/and the second elongated edge member 316 that protrudes laterally outwardly from an area encompassed by the first elongated edge member 314 or/and the second elongated edge member 316 and the spine member 310.

FIG. 4C schematically illustrates a top view of the exemplary prostatic implant 300 shown in FIG. 4A, in a fully non-stressed configuration, highlighting a cranial-nose portion 340 thereof and a caudal-nose portion 342 thereof.

In exemplary embodiments, for example, as shown in FIG. 4C, at least one of the first and second elongated edge members 314 and 316, respectively, has a cranial-nose portion, for example, cranial-nose portion 340, shaped and configured for resting against a ledge imposed by a urinary bladder neck segment adjacent the prostatic urethra (e.g., 108 in FIG. 1A), so as to prevent cranial dislodgement of the prostatic implant 300 into the urinary bladder (e.g., 102 in FIG. 1A), when the spine member 310 engages an anterior interlobar groove (e.g., 118 in FIG. 1C) that extends between the prostatic lateral lobes (e.g., 114a and 114b in FIGS. 1C, 3A, 3B), and when the first and second elongated edge members 314 and 316, respectively, engage corresponding posterolateral interlobar grooves (e.g., 120a and 120b in FIGS. 1C, 3A, 3B). In such exemplary embodiments, the cranial-nose portion 340 is "L" shaped. In exemplary embodiments, for example, as also shown in FIG. 4C, at least one of the first and second elongated edge members 314 and 316, respectively, has a caudal-nose portion, for example, caudal-nose portion 342, shaped and configured for resting against a narrowing imposed by the external urethral sphincter adjacent to the verumontanum of the prostatic urethra, so as to prevent caudal migration of the prostatic implant 300 through the external sphincter and into the bulbar urethra, when the spine member 302 engages an anterior interlobar groove (e.g., 118 in FIG. 1C) that extends between the prostatic lateral lobes (e.g., 114a and 114b in FIGS. 1 C, 3A, 3B), and when the first and second elongated edge members 314 and 316, respectively, engage corresponding posterolateral interlobar grooves (e.g., 120a and 120b in FIGS. 1C, 3A, 3B). In such exemplary embodiments, the caudal-nose portion 342 is "L" shaped.

FIG. 5 schematically illustrates the exemplary prostatic implant shown in FIG. 4C, highlighting inclusion therein of a plurality of exemplary tissue support members 350, 352, 354, and 356, where each such tissue support member is configured as a rib or rib-type member.

FIG. 6 schematically illustrates the exemplary prostatic implant shown in FIG. 4C, highlighting inclusion therein of a pair of exemplary first and second tissue support members 360 and 362, with each such tissue support member including a tissue contacting surface, for example, first and second tissue contacting surfaces 364 and 366, respectively.

In exemplary embodiments, at least one of the tissue support members, for example, at least one of the first and second tissue support members 322 and 324, respectively, or/and rib or rib-type tissue support member 318, includes a tissue contacting surface, such as tissue contacting surface 364 or 366, sized or/and shaped according to dimensions of a portion of a prostatic lateral lobe (for example, left or right prostatic lateral lobe 114a or 114b, respectively, shown in FIGS. 1C, 3A, 3B).

An aspect of some embodiments of the present invention is a system (herein, also referred to as a prostatic implant system) for retracting or/and supporting periurethral tissue enclosing a prostatic urethra along a length of prostate lobes. In exemplary embodiments, the prostatic implant system, in a non-limiting manner, includes: an implant (prostatic implant), and an implant (prostatic implant) manipulator detachably connected to the implant (prostatic implant). Therein, the prostatic implant includes a plurality of elongated edge members interconnected in a form of a collapsible-expandable frame expandable to retract or/and support periurethral tissue by exerting pushing forces upon interlobar grooves located along the prostatic urethra. Additionally, therein, a first one of the elongated edge members includes a first craniolateral corner and a first caudolateral corner, and a second one of the elongated edge members includes a second craniolateral corner opposing the first craniolateral corner and a second caudolateral corner opposing the first caudolateral corner. In such exemplary embodiments, the implant manipulator is configured to manipulate and force the implant first and second caudolateral corners into close proximity with each other.

Any of the hereinabove illustratively described exemplary embodiments of an implant (prostatic implant), such as exemplary prostatic implant 200 or exemplary prostatic implant 300, for retracting or/and supporting periurethral tissue enclosing a prostatic urethra along a length of prostate lobes may be included as part of, and used for implementing, the herein disclosed exemplary embodiments of a system (prostatic implant system) for retracting or/and supporting periurethral tissue enclosing a prostatic urethra along a length of prostate lobes.

Figure 7A:
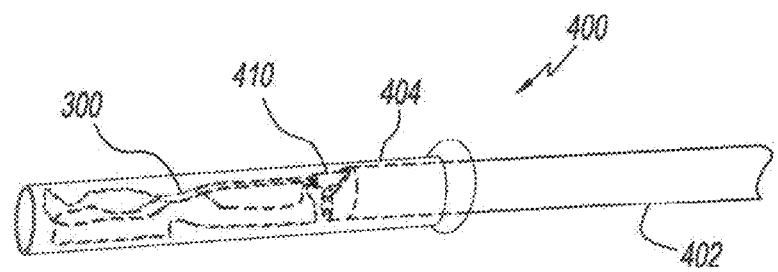

For example, reference is made to FIG. 7A which schematically illustrates an exemplary embodiment of a system (prostatic implant system), indicated as, and referred to by, reference number 400, for retracting or/and supporting periurethral tissue enclosing a prostatic urethra along a length of prostate lobes, highlighting some system components. Therein, an exemplary prostatic implant (such as prostatic implant 300 shown in FIGS. 4A and 4C), in a stressed (e.g., bent contracted or/and compressed, folded type) configuration and operatively connected to the distal end of an exemplary cystoscope 402, is entirely held within an exemplary compression sleeve 404 by an implant manipulator 410 (also described below and shown in more details in FIGS. 8E-8G, and 9).

With reference to FIG. 7A, and FIGS. 4A-4C, exemplary prostatic implant system 400, in a non-limiting manner, includes: an implant (prostatic implant) 300, and an implant (prostatic implant) manipulator 410 detachably connected to the prostatic implant 300. Therein, the prostatic implant 300 includes a plurality of elongated edge members, for example, first and second elongated edge members 314 and 316, respectively, interconnected in a form of a collapsible-expandable frame expandable to retract or/and support periurethral tissue by exerting pushing forces upon interlobar grooves located along the prostatic urethra (e.g., as illustratively described hereinabove with reference to FIGS. 1A-1C, and 3A-3B). Additionally, therein, the first elongated edge member 314 includes a first craniolateral corner 304a and a first caudolateral corner 308a, and the second elongated edge member 316 includes a second craniolateral corner 304b opposing the first craniolateral corner 304a and a second caudolateral corner 308b opposing the first caudolateral corner 308a. In such exemplary embodiments, the implant manipulator 410 (e.g., FIGS. 8E-8G) is configured to manipulate and force the prostatic implant first and second caudolateral corners 308a and 308b, respectively, into close proximity with each other.

Figure 7B:
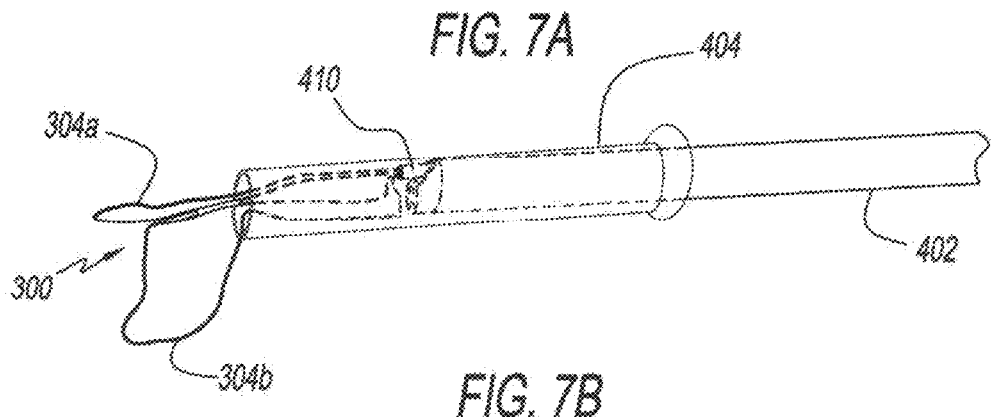
Figure 7C:
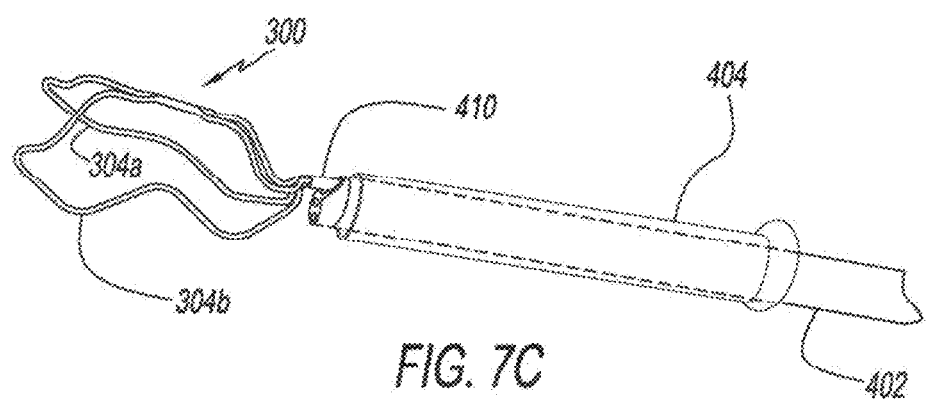
Figure 7D:
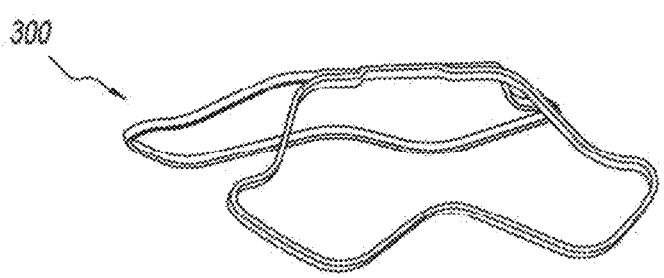

Additional exemplary and optional technical features, characteristics, and properties, as well as exemplary implementation and use, of a system, for example, prostatic implant system 400, for retracting or/and supporting periurethral tissue enclosing a prostatic urethra along a length of prostate lobes, according to some embodiments of the invention, are illustratively described as follows. FIGS. 7B-7C schematically illustrate exemplary embodiments of the prostatic implant system 400, highlighting progressive (sequential) stages of operation thereof, wherein the exemplary prostatic implant 300 is deployed via progressively (sequentially) being pushed out of the compression sleeve 404 by the implant manipulator 410, along with undergoing a type of unfolding of at least some of its structural members. At first (FIG. 7B), distal retractor 302 emerges and then immediately unfolds, at least partly, while the other part of implant 300 is held folded and compressed in compression sleeve 404; followed by (FIG. 7C) complete extraction of implant 300 from within compression sleeve 404, where implant 300 is unfolded at least partly along most or all its entire length. FIG. 7D schematically illustrates the exemplary prostatic implant 300, following deployment by the prostatic implant system 400, in a 'stand-alone' non-stressed, unfolded and expanded configuration after exiting the compression sleeve 404 and detachment from the implant manipulator 410.

In exemplary embodiments of prostatic implant system 400, the implant manipulator 410 (e.g., FIGS. 8E-8G) is configured for progressively (sequentially) changing the shape or form of the prostatic implant 300 according to different progressive or sequential implant deployment configurations, including at least one of the following.

A fully collapsed delivery configuration, whereby the implant first and second craniolateral corners 304a and 304b, respectively, are in close proximity with each other, and, the implant first and second caudolateral corners 308a and 308b, respectively, are in close proximity with each other, for example, as shown in FIG. 7A. In exemplary embodiments, such a fully collapsed delivery configuration of the prostatic implant 300 corresponds to a fully folded configuration, whereby at least some of the prostatic implant structural members are in a type of a fully folded form.

A partially collapsed positioning configuration, whereby the implant first and second craniolateral corners 304a and 304b, respectively, are distanced apart from each other, and, the implant first and second caudolateral corners 308a and 308b, respectively, are in close proximity with each other, for example, as shown in FIG. 7B. In exemplary embodiments, such a partially collapsed positioning configuration of the prostatic implant 300 corresponds to a partially folded/partially unfolded configuration, whereby at least some of the prostatic implant structural members are in a type of a partially folded form while at least some others of the prostatic implant structural members are in a type of a partially unfolded form. In exemplary embodiments, the partially collapsed positioning configuration includes the prostatic implant 300 having a frustum or cone-like shape whose distal-most diameter thereof is greater than the smallest cross-sectional dimension in a urinary bladder neck joining the prostatic urethra (e.g., 108 and 106, respectively, in FIG. 1A), and whose proximal-most diameter thereof is smaller than the smallest cross-sectional dimension in the urinary bladder neck.

An expanded deployed configuration, whereby the implant first and second craniolateral corners 304a and 304b, respectively, are distanced apart from each other, and, the implant first and second caudolateral corners 308a and 308b, respectively, are distanced apart from each other, for example, as shown in FIGS. 7C and 7D. In exemplary embodiments, such an expanded deployed configuration of the prostatic implant 300 corresponds to a fully unfolded configuration, whereby at least most or all, of the prostatic implant structural members are in a type of a fully unfolded form.

In exemplary embodiments, the implant manipulator 410 (e.g., FIGS. 8E-8G), when connected to the prostatic implant 300, is configured for applying thereto at least one of rotational forces, pulling forces, and pushing forces. The implant manipulator 410 applies such forces to the prostatic implant 300 so as to facilitate and effect preceding illustratively described progressive (sequential) changing of the shape or form of the prostatic implant 300, according to the different progressive or sequential prostatic implant deployment configurations.

In exemplary embodiments, the implant manipulator 410 includes a tubular member, for example, tubular member 412, and a tether, for example, tether 414, releasably intertwined through both of the implant first and second caudolateral corners. In such exemplary embodiments, the implant manipulator 410 is configured for continuously or/and selectively pulling the prostatic implant 300 via an operator using the tether 414 against a distal end 416 of the tubular member 412.

Figure 8A:
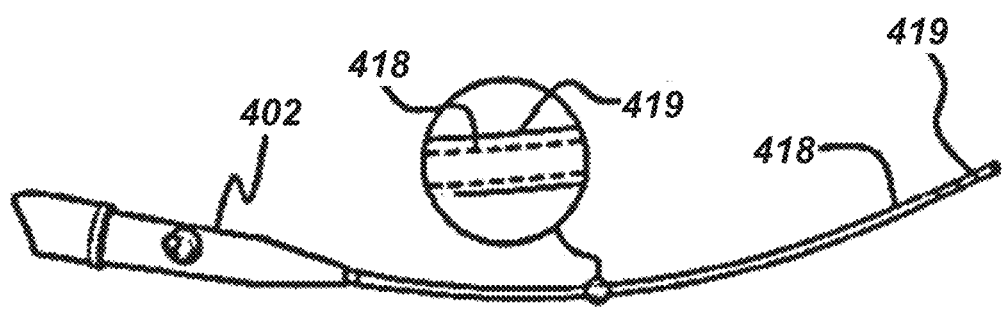
Figure 8B:
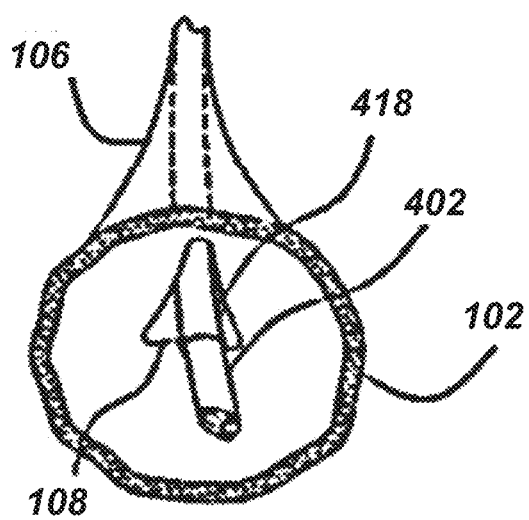
Figure 8C:
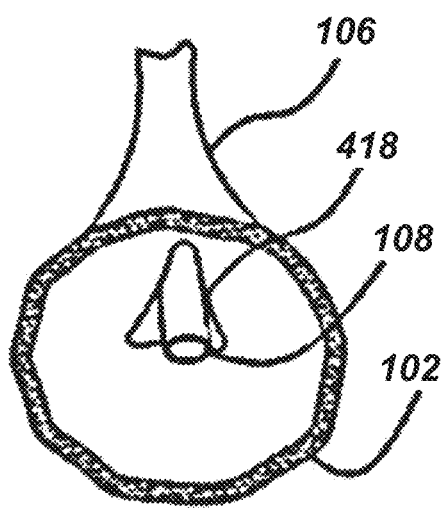

In exemplary embodiments, the prostatic implant system 400 additionally includes an over-sheath, for example, over-sheath 418 shown in FIGS. 8A-8C, sized for covering a length of the cystoscope 402 having a cystoscope lumen (e.g., as a type of "working channel") dimensioned to restrain the prostatic implant 300 in the fully collapsed delivery configuration (e.g., FIG. 7A) via at least encircling the implant first and second craniolateral corners.

In such exemplary embodiments, the implant manipulator 410 is configured for manipulating and shifting the prostatic implant 300 within the over-sheath lumen between the fully collapsed (fully folded) delivery configuration (FIG. 7A) and the partially collapsed (and partially unfolded) positioning configuration (FIG. 7B). Such manipulating and shifting is effected by the implant manipulator 410 pushing or pulling the prostatic implant 300 relative to the over-sheath lumen until the implant first and second craniolateral corners 304a and 304b, respectively, are released from the implant manipulator over-sheath 418. Additionally, in such exemplary embodiments, the implant manipulator 410 is configured for manipulating and shifting the prostatic implant 300 between the partially collapsed (and partially unfolded) delivery configuration (FIG. 7B) and the expanded (and partially or fully unfolded along most/all implant 300 length) deployed configuration (FIGS. 7C, 7D). Such manipulating and shifting is effected by the implant manipulator 410 detaching from the prostatic implant 300 after release of the tether 414 from the implant first and second caudolateral corners 308a and 308b, respectively.

As stated above, any of the hereinabove illustratively described exemplary embodiments of an implant (prostatic implant) for retracting or/and supporting periurethral tissue enclosing a prostatic urethra along a length of prostate lobes may be included as part of, and used for implementing, the herein disclosed exemplary embodiments of a system (prostatic implant system) for retracting or/and supporting periurethral tissue enclosing a prostatic urethra along a length of prostate lobes.

Thus, with reference again made to FIG. 7A, and FIGS. 4A-4C, in exemplary embodiments of prostatic implant system 400, the prostatic implant 300 includes: an elongated spine member 310 having a spinal longitudinal axis 312, and, first and second elongated edge members 314 and 316, respectively, symmetrically opposing each other relative to the spinal longitudinal axis 312, and interconnected to the spine member 310 via at least one interconnecting member 320. In such exemplary embodiments, the spine member 310 has a length being equal to or less than length of an anterior interlobar groove (e.g., 118 in FIGS. 1C, 3A, 3B) that extends between prostatic lateral lobes (e.g., left and right prostatic lateral lobes 114a and 114b, respectively, in FIGS. 1 C, 3A, 3B), or/and substantially less than length of each of the first and second elongated edge members 314 and 316, respectively.

Further, in such exemplary embodiments of prostatic implant system 400 including prostatic implant 300, with additional reference made to FIGS. 1C, 3A, and 3B, the first elongated edge member 314 is sized for positioning in a left posterolateral interlobar groove 120a that extends between a left prostatic lateral lobe 114a and a prostatic medial lobe 116, and the second elongated edge member 316 is sized for positioning in a right posterolateral interlobar groove 120b that extends between a right prostatic lateral lobe 114b and the prostatic medial lobe 116.

Further, in such exemplary embodiments of prostatic implant system 400 including prostatic implant 300, at least one of the implant first and second craniolateral corners 304a and 304b, respectively, are shaped and configured for resting 1710 (for example see FIG. 17) against a ledge imposed by the urinary bladder neck (e.g., 108) so as to prevent cranial dislodgement of the prostatic implant 300 into the urinary bladder (e.g., 102), when the spine member 310 engages an anterior interlobar groove (e.g., 118) that extends between prostatic lateral lobes (e.g., 114a and 114b), and when the first and second elongated edge members 314 and 316, respectively, engage corresponding posterolateral interlobar grooves (e.g., 120a and 120b).

Further, in such exemplary embodiments of prostatic implant system 400 including prostatic implant 300, at least one of the implant first and second caudolateral corners 308a and 308b, respectively, are shaped and configured for resting against a narrowing imposed by the external urethral sphincter adjacent the verumontanum of the prostatic urethra, so as to prevent caudal shift of the prostatic implant 300, when the spine member 310 engages an anterior interlobar groove (e.g., 118) that extends between prostatic lateral lobes (e.g., 114a and 114b), and when the first and second elongated edge members 314 and 316, respectively, engage corresponding posterolateral interlobar grooves (e.g., 120a and 120b). In such exemplary embodiments, each of the implant first and second caudolateral corners 308a and 308b, respectively, has a shape or form of a proximally directed apex, wherein the apex is formed by intersection of converging curved slopes of respective ones of the implant first and second caudolateral corners 308a and 308b, respectively.

An aspect of some embodiments of the present invention is a method (herein, also referred to as a prostatic implant method) for retracting or/and supporting periurethral tissue enclosing a prostatic urethra along a length of prostate lobes.

In exemplary embodiments, the prostatic implant method, in a non-limiting manner, includes:
  Providing an implant along a chosen length of the prostate lobes.
  Exerting continuous radially directed pushing forces upon the anterior interlobar groove between the prostate lobes, and upon at least one of the left and right posterolateral interlobar grooves between the prostate lobes, thereby anchoring the implant in-place.
  Exerting lateral pressing forces upon one or more of prostatic lateral lobes, thereby retracting or/and supporting the periurethral tissue.

In alternative exemplary embodiments, the prostatic implant method, in a non-limiting manner, includes:
  Providing an implant in a fully collapsed delivery configuration, the implant includes an independently actuatable distal retractor incorporating first and second craniolateral corners, and an independently actuatable proximal retractor incorporating first and second caudolateral corners, wherein the first and second craniolateral corners are in close proximity to each other, and, the first and second caudolateral corners are in close proximity to each other.
  Passing the implant in the fully collapsed delivery configuration, in a cranial direction in a subjects urethra, into the subjects urinary bladder.
  Expanding, optionally by unfolding, the distal retractor within inner boundaries of the urinary bladder.
  Positioning under vision the implant in the prostatic urethra along the length of the prostate lobes.
  Expanding, optionally by unfolding, the proximal retractor so as to effect changing the configuration of the implant from the fully collapsed (fully folded) delivery configuration, into an expanded (fully unfolded) deployed configuration wherein the first and second craniolateral corners are distanced apart from each other, and, the first and second caudolateral corners are distanced apart from each other. In some embodiments, unfolding or/and expanding of the implant is two-fold or/and multi-dimensional, for example by unfolding from a collapsed-thin form to larger, radially-expanded, size, in parallel to or followed by lateral expansion thereof.

Any of the hereinabove illustratively described exemplary embodiments of an implant (prostatic implant), such as exemplary prostatic implant 200 or exemplary prostatic implant 300, and any of the hereinabove illustratively described exemplary embodiments of a system (prostatic implant system), such as exemplary prostatic implant system 400, for retracting or/and supporting periurethral tissue enclosing a prostatic urethra along a length of prostate lobes, may be included as part of, and used for implementing, the herein disclosed exemplary embodiments of a method (prostatic implant method) for retracting or/and supporting periurethral tissue enclosing a prostatic urethra along a length of prostate lobes.

For example, reference is made to FIGS. 8A-8L, 9 and 10 which schematically illustrate various stages of delivering and deploying an exemplary prostatic implant, such as prostatic implant 300 illustratively described hereinabove and shown in FIGS. 4A, 4C, and 7D, for retracting or/and supporting periurethral tissue enclosing a prostatic urethra along a length of prostate lobes, using an exemplary system, such as prostatic implant system, such as prostatic implant system 400 illustratively described hereinabove and shown in FIGS. 7A-7C).

As shown in FIG. 8A, over-sheath 418 is sleeved over the longitudinal body 419 of a urological endoscope, particularly, a cystoscope (also known as a lithoscope), for example, cystoscope 402. Then some preliminary steps may be taken by an operator, such as a medical practitioner, in order to scan the treatment area or/and to measure patient-specific anatomical dimensions, optionally, in order to select an implant of proper size for a chosen result.

With reference to FIG. 8B, over-sheath 418, together with cystoscope 402, is then extended throughout the length of the prostatic urethra 106, where the cystoscope distal end 420 is provided adjacent to or inside of the urinary bladder 102. In FIG. 8B, the prostatic urethra 106, the urinary bladder 102, and the bladder neck 108, are drawn for illustrative purposes only, and, in a non-limiting manner, may be considered 'simulated analogs' of the corresponding bodily organs or parts, namely, prostatic urethra 106, urinary bladder 102, and bladder neck 108, schematically shown in FIGS. 1A-1C.

Figure 8D:
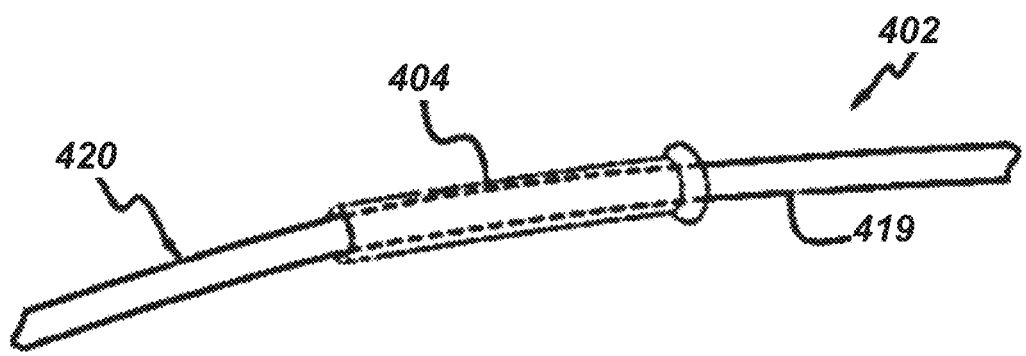

Cystoscope 402 is removed from the prostatic urethra 106 while, optionally, keeping over-sheath 418 in place (as shown in FIG. 8C). Optionally, compression sleeve 404 is then loaded over cystoscope outer periphery 420 (as shown in FIG. 8D), in preparation of loading prostatic implant 300 into the cystocope 402 and collapsing of the prostatic implant 300 using the compression sleeve 404. In order to collapse (e.g., via folding) the prostatic implant 300 from being in a non-stressed fully opened configuration to being in a fully collapsed (fully folded) delivery configuration, and insert prostatic implant 300 into the working channel 422 of the cystoscope 402, a tether 414, is first intertwined (unless it is readily provided as such), optionally, releasably, through both the first and second craniolateral corners 304a and 304b, respectively, of distal retractor 302 of implant 300. First and second craniolateral corners are then urged the into close proximity to each other, so as to effect changing of the prostatic implant 300 into the partially collapsed (partially folded/partially unfolded) positioning configuration, by pulling tether 414 against the distal end 416 of the tubular member 412.

Figure 8E:
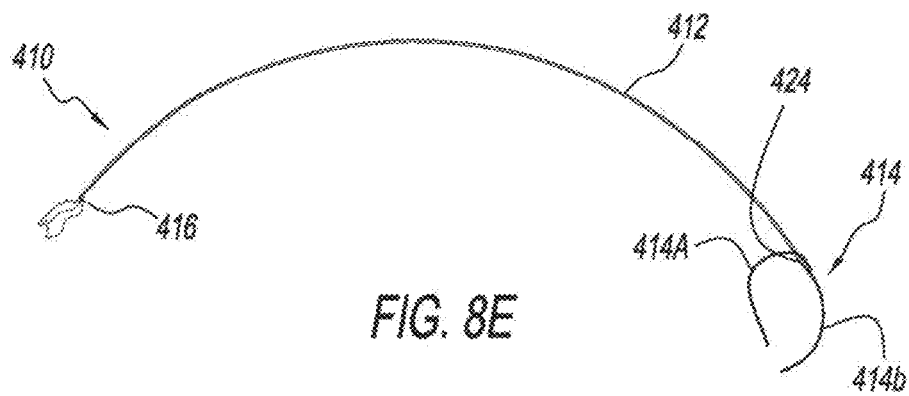

The implant manipulator 410, which can assist in exemplary subsequent steps, such as of implant delivery, positioning or/and activating, can be formed by threading tether 414 through the lumen of the tubular member 412, and optionally fixating proximal end (e.g., proximal both free ends 414a and 414b) of tether 414 relative to the proximal end 424 of tubular member 412. FIG. 8E demonstrates an exemplary formation of the implant manipulator 410 connected with the prostatic implant 300, also forcing it into the partially collapsed (partially folded/partially unfolded) positioning configuration.

Figure 8F:
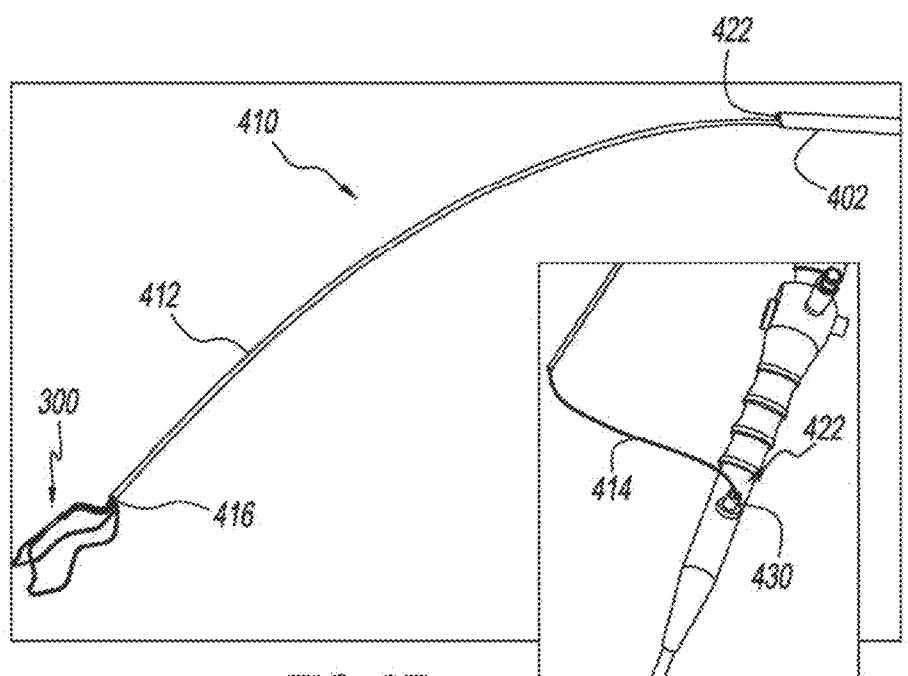
Figure 8G:
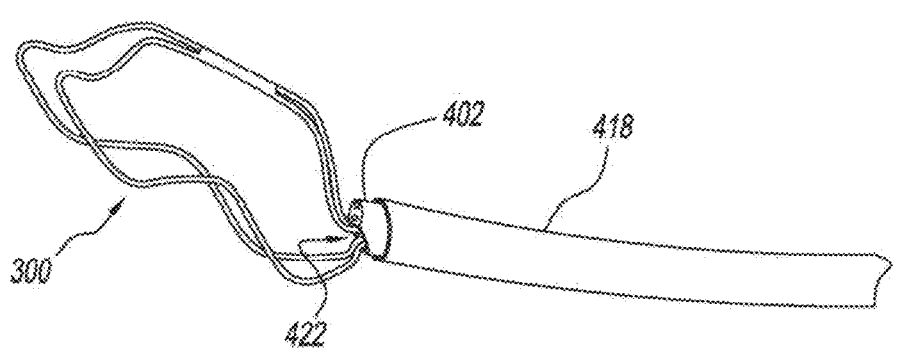

As shown in FIG. 8F, the implant manipulator 410, with the prostatic implant 300 connected thereto, are then loaded into a lumen (e.g., working channel 422) of the cystoscope 402. Optionally, the proximal end of the implant manipulator 410 is passed into the distal opening of the working channel 422 (FIG. 8F(i)), while the proximal end of the implant manipulator 410 is drawn from a proximal opening 430 of the working channel 422 (FIG. 8F(ii)). FIG. 8G shows the prostatic implant 300 in its partially collapsed (partially folded/partially unfolded) positioning configuration coupled to the cystoscope 402 using the implant manipulator 410 (not shown, fully inserted within working channel 422).

Figure 8H:
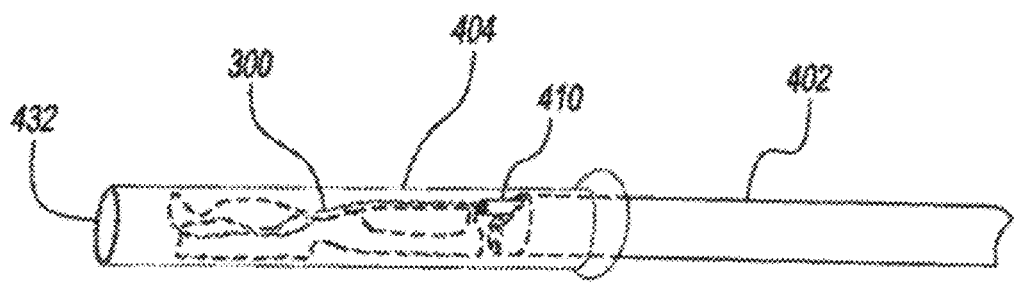
Figure 8I:
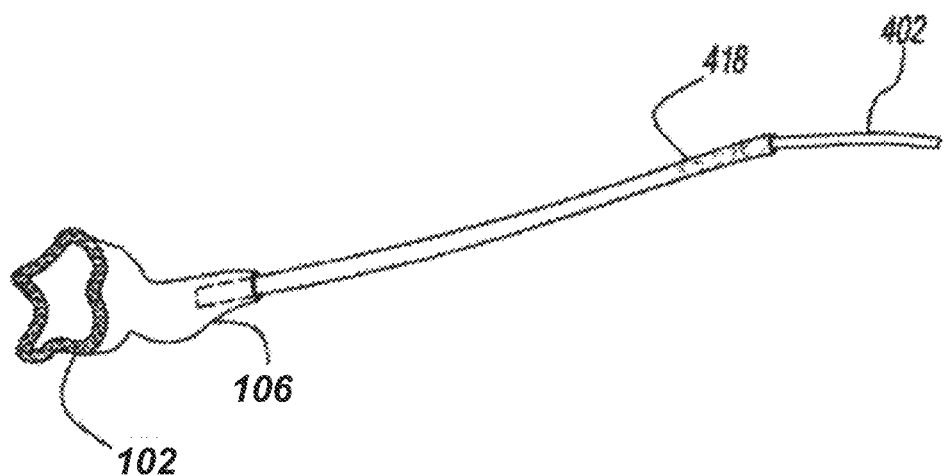

As shown in FIG. 8H, the prostatic implant 300 is then forced into a fully collapsed (fully folded) delivery configuration using the compression sleeve 402, by drawing the compression sleeve 404 over entire length of the prostatic implant 300. The compression sleeve 404 incorporates a lumen 432 sized for effecting changing of the configuration of the prostatic implant 300 from the partially collapsed (partially folded/partially unfolded) positioning configuration to the fully collapsed (fully folded) delivery configuration.

Figure 8J:
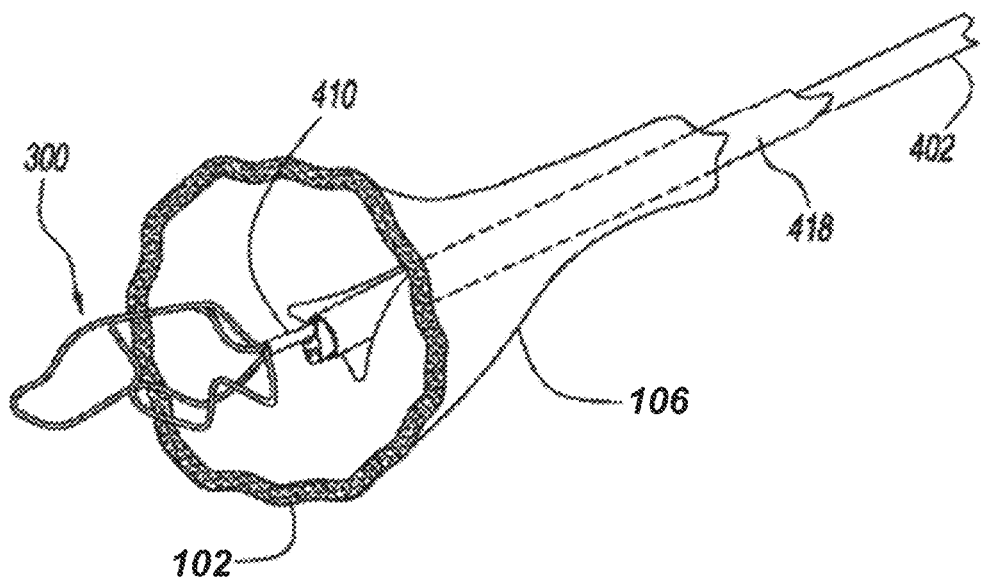

The prostatic implant 300 is then pushed distally through over-sheath 418 with the cystoscope 402 (FIG. 8I) and passed, still in its fully collapsed (fully folded) delivery configuration, in a cranial direction in the prostatic urethra 106, into the urinary bladder 102 of the subject Then, the prostatic implant distal retractor 302 is released from its restricting boundary, namely, the working channel 422 and the over-sheath 418, until at least the distal retractor 302, and, optionally, also the proximal retractor 306, protrudes in a cranial direction from the prostatic urethra 106 (as shown, for example, in FIG. 8J). This may be effected by either pushing the prostatic implant 300, optionally relative to the over-sheath 418, or/and the cystoscope 402 further into the urinary bladder 102, or by holding the prostatic implant 300 in the urinary bladder 102, using the implant manipulator 410, while proximally pulling over-sheath 418 or/and the cystoscope 402.

Releasing the prostatic implant 300 should effect expansion of the distal retractor 302 within inner boundaries of the urinary bladder 102 into the partially collapsed (partially folded/partially unfolded) positioning configuration, resulting in the first and second craniolateral corners 304a and 304b, respectively, being distanced apart from each other, and, the first and second caudolateral corners 308a and 308b, respectively, being kept in close proximity to each other.

Figure 8K:
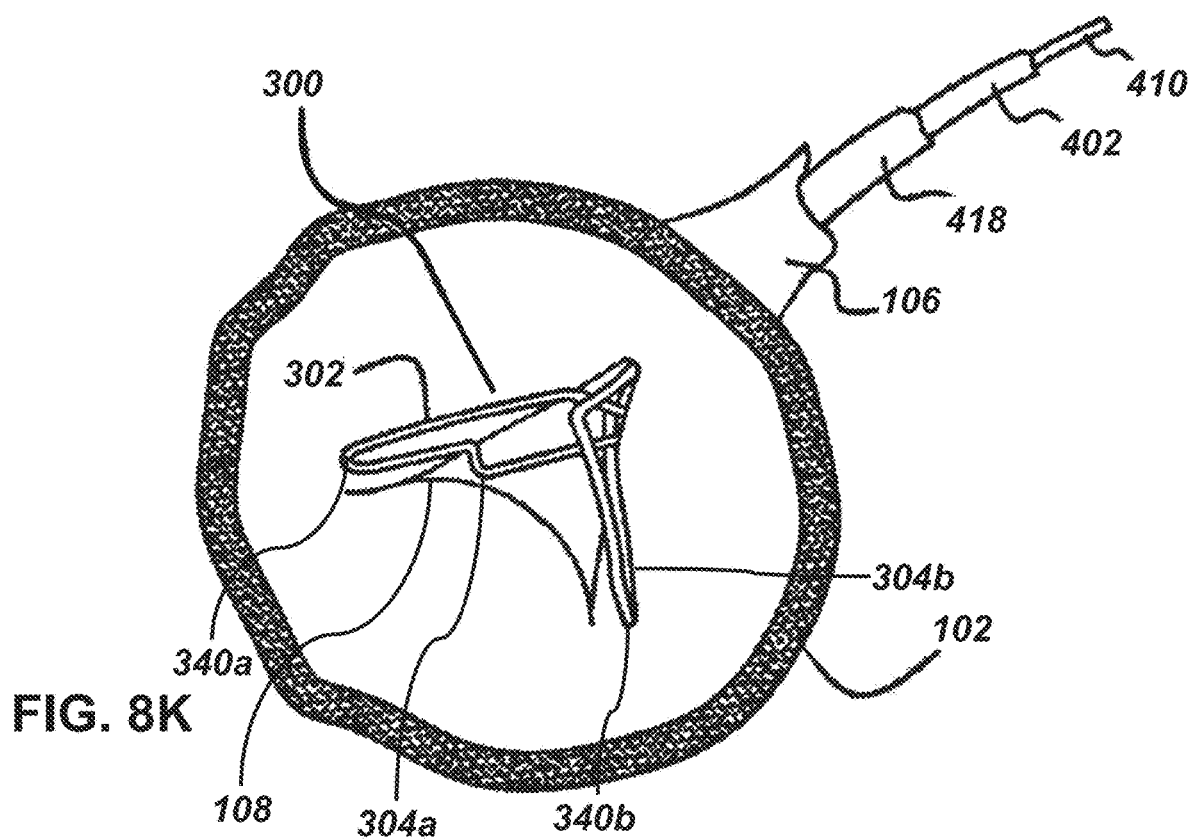

Then, under vision, using the cystoscope 402, the prostatic implant 300 is positioned in the prostatic urethra 106 along the length of the prostate lobes, as shown in part, in FIG. 8K. The prostatic implant 300 positioning in the prostatic urethra 106 may include at least one of the following steps, not necessarily in same order Rotating the prostatic implant 300, by applying torque forces, relative to the spinal longitudinal axis 312 so as to align the spine member 310 with the anterior interlobar groove of the prostatic urethra 106, or/and to align the first elongated edge member 314 with the left posterolateral interlobar groove of the prostatic urethra 106, or/and to align the second elongated edge member 316 with the right posterolateral interlobar groove of the prostatic urethra 106.

Pulling the prostatic implant 300 in a caudal direction to a position within the prostatic urethra 106 or/and placing 1910 (e.g. see FIG. 19) the first and second craniolateral corners 304a and 304b, respectively, against a narrowing imposed by the internal urethral sphincter adjacent to the urinary bladder neck 108.

Inserting the spine member 310 in the anterior interlobar groove of the prostatic urethra 106, or/and inserting the first elongated edge member 314 in the left posterolateral interlobar groove of the prostatic urethra 106, or/and inserting the second elongated edge member 316 in the right posterolateral interlobar groove of the prostatic urethra 106.

Visually verifying the alignment using cystoscopy (with the cystoscope 402).

Figure 8L:
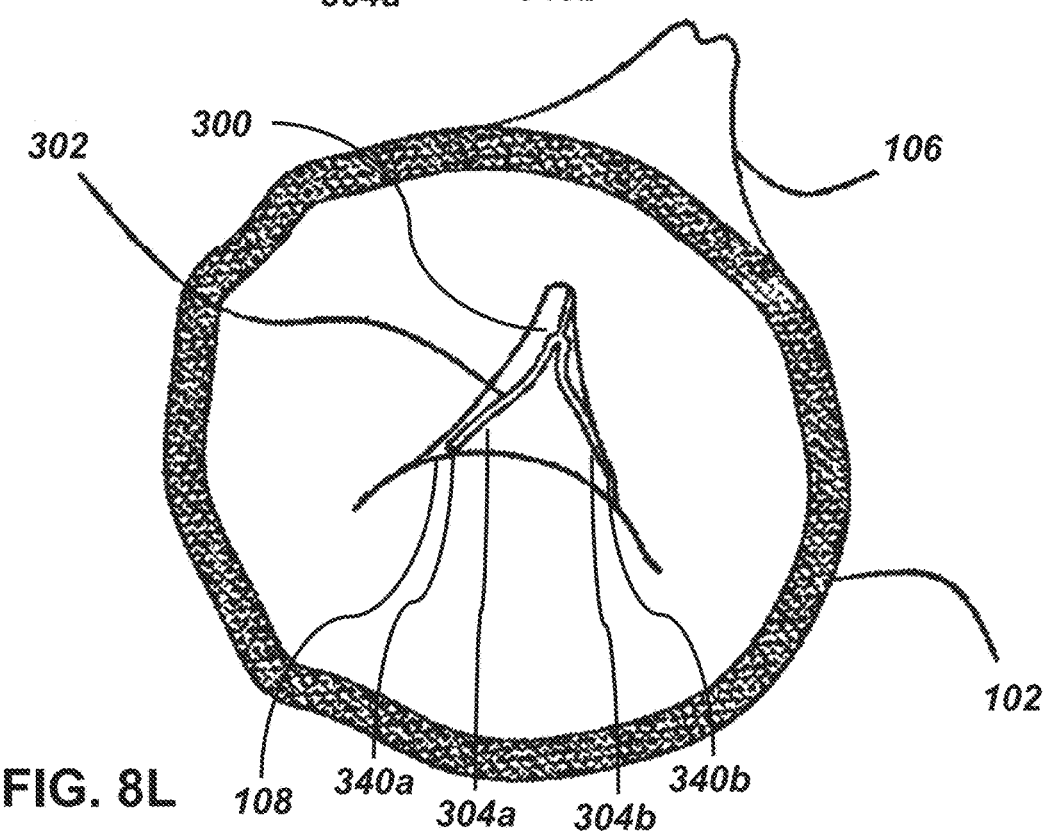

The prostatic implant 300 positioning should result, if the prostatic implant 300 is in its partially collapsed (partially folded/partially unfolded) positioning configuration, in effecting expansion of a distal region of the prostatic urethra 106, using the distal retractor 302, into a greater lumen size than an adjacent proximal region of the prosthetic urethra 106. The distal retractor 302 may also be partially collapsed into conformity with anatomy of the distal region of the prostatic urethra 106. FIG. 8L provides a frontal (caudally directed) view for an exemplary representation of proper positioning of the prostatic implant 300 within the prostatic urethra 106. By also expanding (unfolding) the proximal retractor 306, the configuration of the prostatic implant 300 can be changed from the fully collapsed (fully folded) delivery configuration into an expanded (fully unfolded) deployed configuration. Optionally, in exemplary embodiments, such expansion (unfolding) of the prostatic implant 300 is effected in a partial manner, whereby at least most but not necessarily all, of the prostatic implant 300 structural members change into a fully expanded (unfolded) configuration, for example, possibly due to physical size and dimensional restrictions imposed by the in-vivo environment of the periurethral tissue and the surrounding prostatic lobes. The expansion (unfolding) procedure results in the first and second craniolateral corners 304a and 304b, respectively, to become distanced apart from each other, and, the first and second caudolateral corners 308a and 308b, respectively, to become distanced apart from each other as well. The first and second tissue support members 322 and 324, respectively, of the prostatic implant 300 are also released for supporting respective portions of the lateral prostatic lobes following implant positioning.

The cystoscope 402 is then removed from the prostatic urethra 106, and from the entire urethra of the subject while keeping the over-sheath 418 in place.

Any of the hereinabove illustratively described steps or procedures of the herein disclosed exemplary embodiments of a method (prostatic implant method) for retracting or/and supporting periurethral tissue enclosing a prostatic urethra along a length of prostate lobes, may be repeated in case there is a need to change (e.g., correct) positioning of the prostatic implant 300, or of any portion or member thereof, in relation to chosen anatomical or/and physiological considerations. Repeating any of the previous steps may include, be preceded by, or be followed by, re-collapsing the prostatic implant 300 back into the fully collapsed delivery configuration or/and passing the prostatic implant 300 back into the urinary bladder 102. Repeating may be persistent until reaching a chosen result. The chosen result can be verified under vision, for example, using the cystoscope 402. The chosen result may include anchoring different portions of the prostatic implant 300 in at least two of the anterior interlobar grooves, the left posterolateral interlobar groove, and the right posterolateral interlobar groove, of the prostatic urethra 106, within the boundaries of the prostate lobes. The chosen result may also include lifting both prostatic lateral lobes so as to enlarge minimal lumen size of the prostatic urethra 106, optionally, to at least 1 mm, or at least 2 mm, along a continuous length of the prostatic urethra, optionally along its entire length, optionally, by shifting each of the prostatic lateral lobes, pivotally, relative to the anterior interlobar groove.

Once it is verified that the prostatic implant 300 is in appropriate positioning within the prostatic urethra 106, final deployment and implantation stages can take place, and the prostatic implant 300 should be left therein, with no further interaction with the implant manipulator 410. Accordingly, the fully deployed and implanted prostatic implant 300 is thereby configured and positioned to continuously exert radially directed pushing forces upon the anterior interlobar groove and at least one of the left and right posterolateral interlobar grooves. This may facilitate preventing or minimizing possible axial or/and rotational movement of the prostatic implant 300, or/and to increase distance separating the superior interlobar grooves and to increase distance separating the left and right inferior-lateral interlobar grooves, Such may also facilitate the prostatic implant 300 to exert lateral pressing forces upon each prostatic lateral lobe, thereby, retracting or/and supporting the periurethral tissue.

Figure 9:
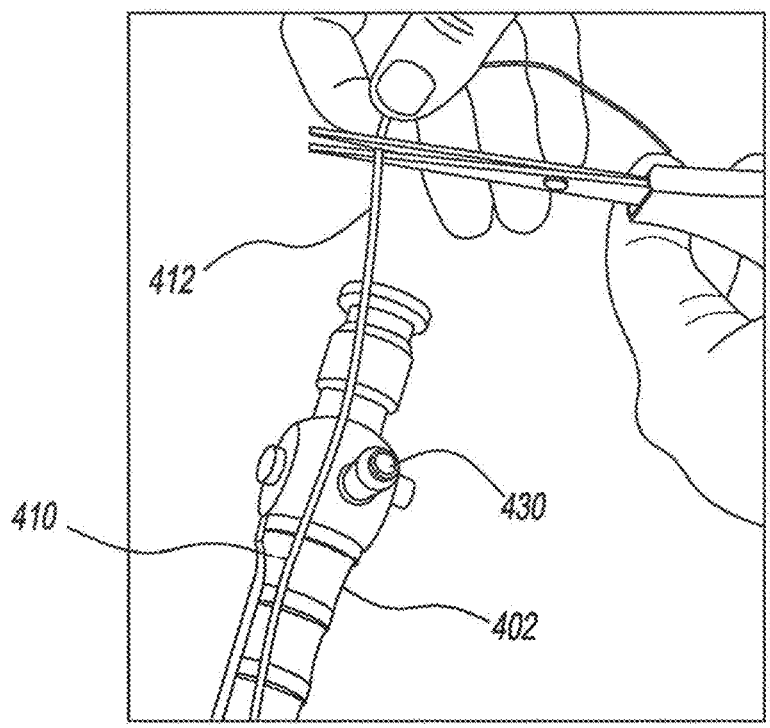
Figure 10:
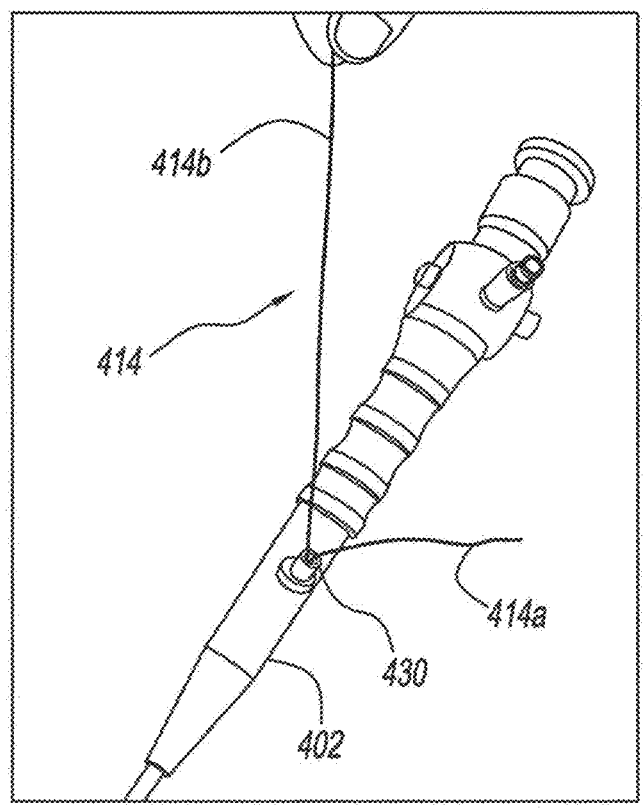

As shown in FIGS. 8A to 8L, 9 and 10, the implant manipulator 410 is taken apart into its main parts, namely, the tubular member 412 and the tether 414 (partly shown in FIG. 10), illustrating scissoring of the implant manipulator 410), and the tether 414 is pulled and withdrawn from holding the prostatic implant 300 and subsequently, from the subject's body (FIG. 9).

FIGS. 1 through 5, wherein like parts are designated by like reference numerals throughout, illustrate a dilating device for the prostatic urethra, and a method of use according to the present invention. Although the present invention will be described with reference to the figures, it should be understood that many alternative forms can embody the present invention. One of ordinary skill in the art will additionally appreciate different ways to alter the parameters disclosed, such as the size, shape, or type of elements or materials, in a manner still in keeping with the spirit and scope of the present invention.

Figure 11A:
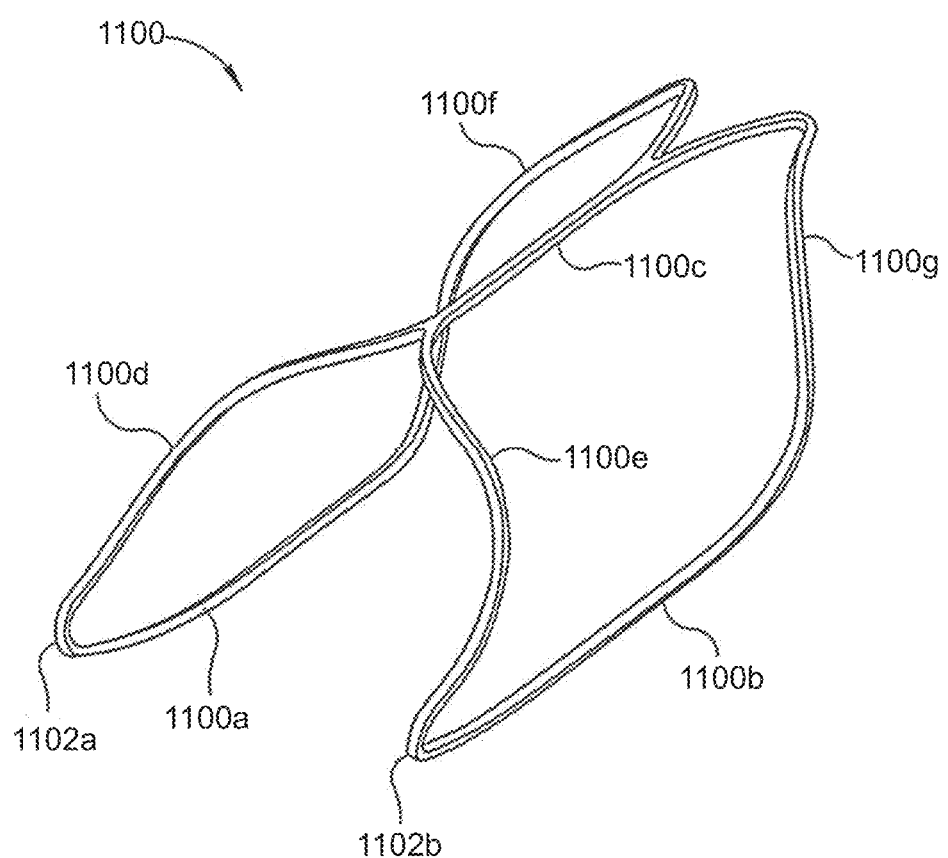
FIG. 11C shows a profile view of the device of FIG. 11A, according to an embodiment.
FIG. 11D shows a frontal view of the device of FIG. 11A, according to an embodiment.
Figure 11B:
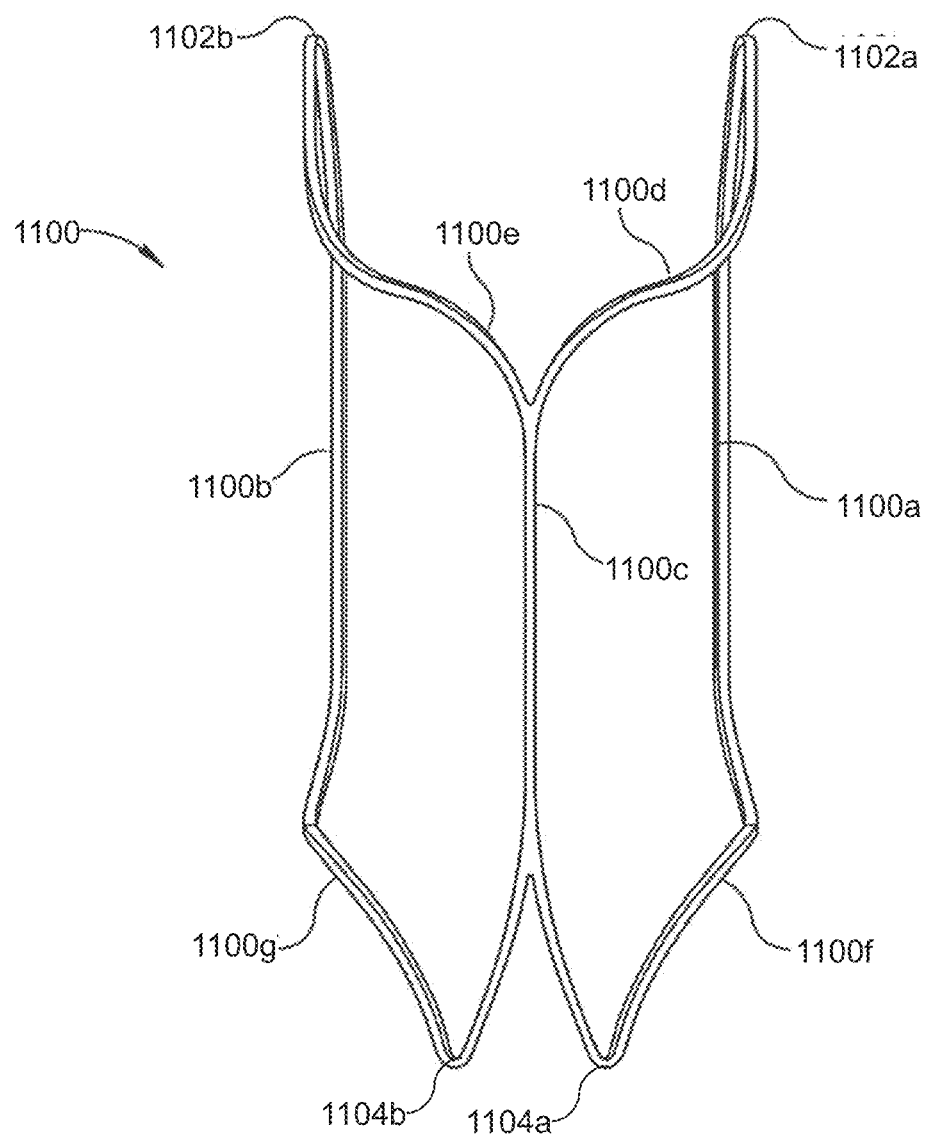

Reference is now made to FIGS. 11A-11B which illustrates a dilating device 1100 for the prostatic urethra, from a perspective view and a top view, respectively, in accordance with an embodiment. Device 1100 may comprise at least three laterally connected ridges 1100a, 1100b, 1100c, each of which is configured to longitudinally engage with a different substantially longitudinal groove of the prostatic urethra of a patient. Device 1100 may be normally-open, and may be configured to laterally compress, causing the distance between ridges 1100a, 1100b, 1100c to decrease, thereby enabling the insertion 1600 (for example FIGS. 16, 17, 18) of device 1100 into the prostatic urethra in a compressed configuration, and to laterally expand to its normally-open configuration, causing the distance between ridges 1100a, 1100b, 1100c to increase, upon deployment within the prostatic urethra. The lateral expansion of device 1100 when deployed within the prostatic urethra may exert a radially outward force that causes ridges 1100a, 1100b, 1100c to engage with the grooves of the urethra and push them outwards, thereby dilating the prostatic urethra, and allowing a free flow of a liquid, such as urine, to pass from the bladder through the urethra and out of the patient's body.

Peripheral ridges 1100a, 1100b may each be configured to engage with a different postero-lateral groove of the prostatic urethra, and central ridge 1100c may be configured to engage with the anterior inter-lobar groove of the prostatic urethra.

Two distal connectors 1100d, 1100e may branch out from a V-shaped distal end of central ridge 1100c and laterally connect to the distal ends of peripheral ridges 1100a and 1100b, respectively. Additionally, two proximal 1100f, 1100g may branch out from a proximal end of central ridge 1100c and laterally connect to the proximal ends of peripheral ridges 1100a, and 1100b, thereby forming two closed forms that are joined at central ridge 1100c. In one embodiment, proximal connectors 1100f and 1100g may branch out from a V-shaped proximal end of central ridge 1100c, as illustrated in FIG. 11A. In the embodiment of FIG. 11A, connectors 1100d, 1100e, 1100f, and 1100g may be substantially S-shaped, forming a butterfly shape by device 1100 when in the normally-open configuration, where proximal connectors 1100f, and 1100g may be configured for positioning towards the caudal end of the prostate urethra and/or distal connectors 1100d, and 1100d may be configured for positioning towards the cranial end of the prostate urethra against the bladder neck.

In some embodiments, a device may be provided with two, or more distally positioned protrusion. For example, protrusions 1102a and 1102b are configured to expand the postero-lateral sides of the prostatic urethra and/or to impinge upward from the cranial end of the prostatic urethra against the postero-lateral side of the bladder neck. In some embodiments, lateral stretching of the urethra forms a ledge. The impinging of the distally positioned protrusions on this ledge and/or the cranial end of the prostatic urethra optionally prevents a migration of device 1100 into the urinary bladder. Protrusions 1102a and 1102b may be integrally formed with distal connectors 1100d, 1100e, such as forming a portion of the S-shape of distal connectors 1100d, 1100e that are shown in FIGS. 11A, 12.

Device 1100 may additionally be configured for alignment 1606 (for example see FIGS. 16 18) within the prostatic urethra via two proximally disposed protrusions 1104a and 1104b that are provided with device 1100 to releasably connect device 1100 to an alignment mechanism provided with the deployment lumen, and which will be described in greater detail below. Protrusions 1104a and 1104b may be integrally formed with proximal connectors 1100f, 1100g.

For example, an operator may be guided by an external marker provided with device 1100, and apply a torque that is transferred to device 1100 and that causes it to rotate, thereby aligning central ridge 1100c with the anterior interlobar groove of the prostatic urethra.

Device 1100 may be integrally formed, and may be made of a suitably flexible material, such as wire or cut foil made of a super-elastic alloy such as Nitinol. Alternatively, device may be made of a super-elastic polymer or biodegradable polymer.

This memory-retaining flexibility may allow distal connectors 1100d and 1100e and proximal connectors 1100f and 1100g to bend in a manner that decreases the distance between ridges 1100a, 1100b and 1100c, thereby compressing device 1100 to enable its insertion into the prostatic urethra. Additionally, distal connectors 1100d and 1100e and proximal connectors 1100f and 1100g may be normally unbent, and may revert to their normally unbent configuration upon deployment within the prostatic urethra, thereby increasing the distance between ridges 1100a, 1100b and 1100c and expanding device 1100 to enable dilating 1612 (for example see FIGS. 16, 17 18) the prostatic urethra.

Figure 11C:
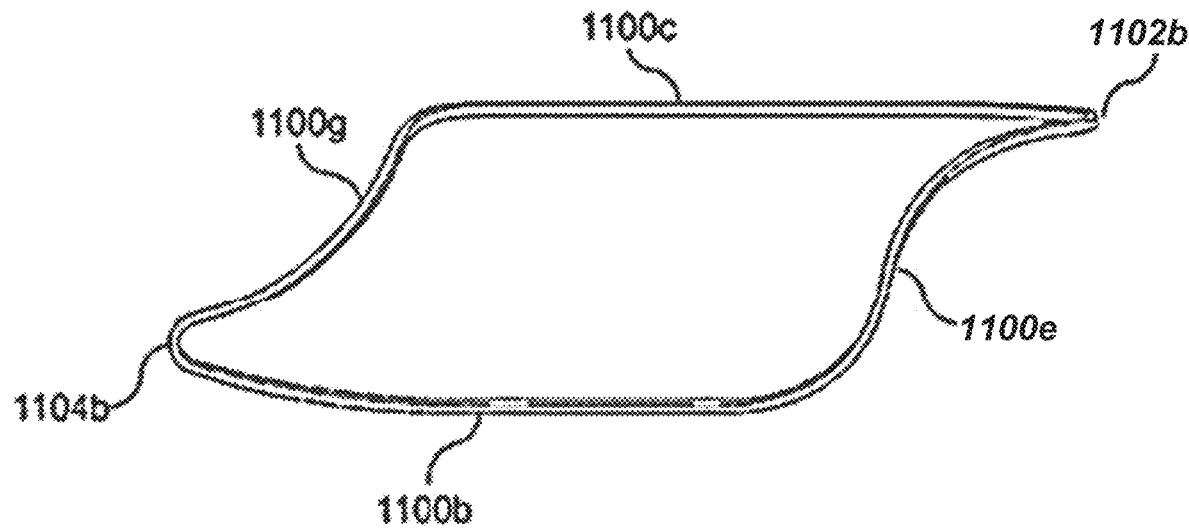

Reference is made to FIG. 11C, which shows a profile view of the device of FIGS. 11A-11B, according to an embodiment. The closed form that is formed by peripheral ridge 1100b, central ridge 1100c, distal connector 1100e, and proximal connector 1100g resembles a 'butterfly wing'. An identical and symmetric butterfly wing (not shown) is formed by peripheral ridge 1100a, central ridge 1100c, distal connector 1100d, and proximal connector 1100f.

Figure 11D:
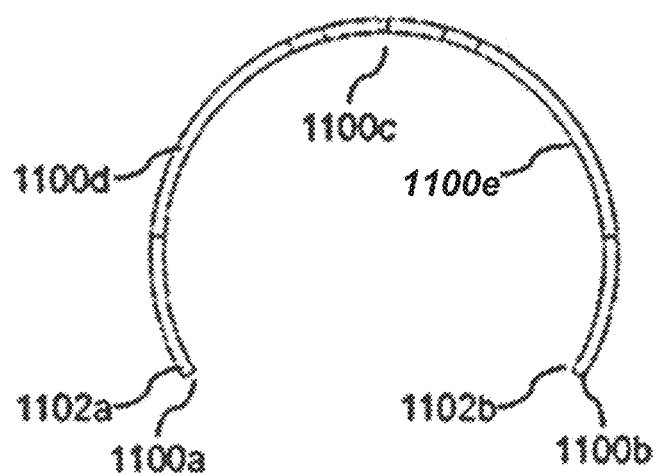

Reference is now made to FIG. 11D, which shows a frontal view of the device of FIGS. 11A-B, according to an embodiment. When normally-open, S-shaped distal connectors 1100d, 1100e, comprising a distal end of device 1100, may be configured to span an arc, such as a portion of a circle to dilate the prostatic urethra at the bladder neck.

In one embodiment, the shape of the device in the normally-open configuration may reside within the delimiting surface of a longitudinally oriented tube, such as a free-form longitudinally-oriented lumen. The shape of the lumen may be a cylinder, prism, or trunk-conical shape, to name a few, and may comprise a combination of shapes. For example, the lumen may have a cylindrical shape at the tubular ends, and a triangular prism shape at the midsection. The profile, or cross section of such shape may be circular ovoid, triangular, and may be uniform or may change in size and/or shape along the axial length. In the example given above, the cross-section at the ends of the open device may be circular due to the normally-open circular arc-shape of connector pairs 1100d, 1100e, and 1100f, 1100g, whereas the cross-section at the middle of the device may be triangular due to the three ridges 1100d, 1100e, 1100c that are 'pulled apart' by the normally open connectors. The device may have a varying cross-sectional size. For example, a portion of the device may reside within a fraction, such as 50%, 66%, or 75% of the longitudinally oriented tube.

Similarly, in the normally-open configuration, S-shaped proximally connectors 1100f, 1100g, comprising a proximal end of device 1100 may be configured to reside within the circular delimiting surface of a cylinder to dilate the prostatic urethra at the proximal end of device 1100.

The device may be shaped for residing within the prostate urethra and for positioning on the longitudinal axis between the external sphincter of the urethra distally and the bladder neck proximally.

In an embodiment, distal connectors 1100d, 1100e with ridge 1100c may, in the normally-open configuration, may create an arc that exerts a lateral force on the lateral prostate lobes and dilates the prostate. For example, distal connectors 1100d and/or 1100e may expand a cranial portion of the prostatic urethra. Similarly, connectors 1100f, 1100g with 1100c may create another arc that exerts a lateral force on the lateral prostate lobes and may dilate the prostate at a region situated caudally. Thus, the device may provide two or more arcs that each exert a lateral force on a different region of the lateral prostate lobes.

In another embodiment additional connectors (not shown), similar and substantially parallel to connectors 1100d, 1100e, 1100f, and 1100g, may be provided to laterally connect each peripheral ridge 1100a, 1100b, to the central ridge 1100c at a point on each ridge that lies between the distal and proximal ends of the peripheral and central ridges 1100a, 1100b, 1100c, such as at a midpoint along the ridge. The distance along the long axis of the device between any such pair of connectors may be between 0.5 cm to 3 cm, or more explicitly between 1 cm to 2 cm. The shape of the device in the normally-open configuration may reside within the delimiting surface of an longitudinally oriented tube, such as a free-form longitudinally-oriented lumen.

In an embodiment, the length of the device may range between 1 cm to 7 cm. There may be different sizes suitable for different lengths of prostate urethra.

In an embodiment, the diameter of the expanded device may be between 10 mm to 30 mm, and more explicitly between 15 mm and 25 mm.

In an embodiment, the device may be compressed to a minimal diameter of 0.5 mm to 3 mm and more explicitly of 1 mm to 2 mm.

In an embodiment, in case of a Nitinol device, the wire or ribs size may range from 0.2 to 0.8 mm and more explicitly between 0.3 mm to 0.6 mm.

In an embodiment, the dilating action of the device on the prostate urethra may be performed by the radial outward force exerted by the longitudinally oriented ridges on the prostate grooves and by an additional force exercised on the lateral lobes by the arc formed by the connection of components 1100d, 1100c, 1100e, and the arc formed by the connection of components 1100f, 1100c, 1100g.

In an embodiment, the components of the device, such as the ridges and connectors, or alternatively, the dilating means and connecting ridges of the device may be configured to maintain intimate contact with the mucosa of the prostate urethra when the device is in the open configuration.

Alternatively, the arcs formed by connectors 1100d, 1100e, 1100f, and/or 1100g of device 1100 may comprise at least two dilating means of the prostate urethra. Connectors 1100d, 1100e, 1100f, and 1100g may be connected with longitudinally oriented ridges 1100a, 1100b, and 1100c. Contact with the mucosa of the prostrate may fix the device in place within the prostate urethra and prevent their movement or dislodgement.

In one embodiment, any of connectors 1100d, 1100e, 1100f, and 1100g may comprise closed rings, and any of connecting ridges may have an oblique or sinusoidal orientation.

Reference is now made to FIGS. 12A-12B, which together show an exemplary deployment of a device for dilating a prostatic urethra, according to an embodiment. FIG. 12A shows a cross-section of prostatic urethra 1200 that is obstructed by an enlarged prostate 1202. FIG. 13B shows the cross-section of the prostatic urethra of FIG. 12A upon deploying a dilating device, in accordance with an embodiment of the invention. The three laterally connected ridges of the device that are illustrated at a midsection view along the axially oriented device and labeled as points 1204a, 1204b, and 1204c, are shown in the normally-open configuration and engaged within the grooves of prostatic urethra 1200, thereby dilating urethra 200 to allow a free passage of fluid therethrough.

Reference is now made to FIGS. 13A-13B which together illustrate an apparatus for deploying a dilating device for the prostatic urethra, in accordance with an embodiment. FIG. 13A shows a dilating device 1300 in the normally-open configuration such as after deployment, and FIG. 13B shows device 1300 in the compressed configuration while housed within a deployment lumen 1308, prior to deployment. The apparatus for deployment and the dilating device may be jointly referred to as a "kit".

Turning to FIG. 13B, to deploy device 1300, deployment lumen 1308 may be retracted relative to device 1300 to expose device 1300 from the distal end 1314 of lumen 1308, allowing device 1300 to protrude from lumen 1308 and expand to its normally-open configuration, as shown in FIG. 13A. Upon protruding from lumen 1308 and during the expansion of device 1300, the ridges of device 1300 may engage with the grooves of the prostatic urethra and cause it to dilate, as described above. To reposition device 1300 within the prostatic urethra after its exposure from lumen 1308, device 1300 may be retracted relative to lumen 1308, such as by pulling a string 1312 that is releasably attached to device 1300 and that is exposed from a proximal end of deployment lumen 1308. The distal opening 1314 of lumen 1308 may press on the expanded ridges of device 1300, causing device 1300 to compress and allowing its retreat into lumen 1308 where it may be housed for subsequent redeployment.

The retraction of either deployment lumen 1308 or device 1300 in relation to each other may be performed mechanically by a practitioner, such as via a work channel of a cystoscope, and which will be described in greater detail below.

Dilating device 1300 may be provided with one or more proximally disposed protrusions 1304a and 1304b that are that may be integrally formed with the proximal end of device 1300 and that are configured to releasably connect device 1300 to an alignment mechanism 1306 that is configured for being housed within deployment lumen 1308.

Alignment mechanism 1306 may comprise an alignment lumen 1310 concentrically housed within deployment lumen 1308, as well as releasable string 1312. String 1312 may 1100p through protrusions 1304a and 1304b of device 1300 and may run through alignment lumen 1310 and may be exposed from a proximal end of alignment lumen 1310 for subsequent removal upon deployment of device 1300. Device 1300 may be configured for alignment within the prostatic urethra via a torque that is transferred from alignment mechanism 1306 to device 1300. For example, an operator may rotate alignment lumen 1310 to align alignment lumen 1310 with an externally provided alignment mark, thereby applying a torque to alignment lumen 1310 that is transferred by alignment mechanism 1306 to device 1300 and causes device 1300 to be aligned within the prostatic urethra.

Alternatively, referring to FIGS. 14A-14B a cystoscope 1420 disposed with a work channel 1422 may be used for deploying device 1300 of FIGS. 13A-B from the distal end 1428 of cystoscope 1420. Device 1300 housed within deployment lumen 1308 and optionally with alignment lumen 1310 may be inserted into work channel 1422. The deployment and alignment of device 1300 may be controlled from a proximal end 1428 of work channel 1422.

In an embodiment, cystoscope 1420 may be provided with a fluid delivery lumen and a balloon (not shown) that are configured to deliver a fluid to inflate the patient's bladder. The device may be configured for delivery into the inflated bladder, where it may be extracted from the deployment lumen to expand within the bladder, and then retracted for final deployment within the prostate urethra.

Reference is made to FIG. 14B which shows a close-up view of distal end 1428 of cystoscope 1420, a camera 1424 and illuminator 1426 provided with cystoscope 1420 may be utilized, in an embodiment, for aligning and deploying device 1300 using conventional techniques. Deployment lumen 1308 housing device 1300 and alignment mechanism 1306, and optionally the fluid delivery lumen and balloon, may be inserted into work channel 1422 of cystoscope 1420 and may be manipulated from a proximal end 1428 of work channel 1422 to deploy device 1300 within the prostatic urethra. The patient's bladder may be filled via the fluid delivery lumen and balloon, allowing deployment of device 1300 within the prostatic urethra via the bladder.

Reference is now made to FIG. 15 which is a flowchart of a method for deploying a dilating device into a prostatic urethra.

The laterally compressed dilating device may by inserted into the urethra of a patient via a deployment lumen that is releasably connected to the device (Step 1500). The patient's bladder may be filled according to conventional techniques, such as via a fluid delivery lumen disposed with a balloon (Step 1502). The device may be extracted from the deployment lumen and inserted into the urinary bladder, such as by retracting the deployment lumen relative to the device, and, upon exiting from the deployment lumen, the dilating device may expand to a normally-open configuration in the partially filled urinary bladder of the patient (Step 1504). A torque may be applied to align the device via an alignment mechanism connected to the device, such as by rotating an alignment lumen of the alignment mechanism and transferring the torque to the device, where alignment may comprise aligning a central ridge of the device for engaging with the anterior inter-lobar groove of the prostatic urethra and aligning two peripheral ridges of the device to each engage with a different postero-lateral groove of the prostatic urethra (Step 1506). The application of the torque may be guided via a cytoscope, or alternatively, via an external mark indicating that the device is aligned.

The aligned device may be positioned in the prostate urethra, such as by pulling on the deployment mechanism to draw the device in from the bladder into the prostate urethra (Step 1508). Two protrusions disposed at the distal end of the device may be caused to impinge against the postero-lateral side of the bladder neck, thereby securing the position of the device, and preventing a migration of the device into the urinary bladder (Step 1510). The device, thus deployed and aligned within the prostatic urethra, may exert an outwards radial force that pushes the inter-lobar grooves of the urethra outwards, and dilate the urethra (Step 1512).

If the positioning or alignment of the device is incorrect, the device may be retracted relative to the deployment lumen, causing the device to laterally compress and retreat within the deployment lumen (Step 1514). The retreated device may be repositioned or realigned within the prostatic urethra and redeployed (Steps 1504-1512). If the positioning and alignment of the device is correct, The device may be disconnected from the deployment and alignment lumens (Step 1518), such as by removing a string that releasably connects the device to the alignment lumen.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is to be understood that the following claims are to cover all generic and specific features of the invention described herein, and all statements of the scope of the invention which, as a matter of language, might be said to fall therebetween.

It is expected that during the life of a patent maturing from this application many relevant technologies will be developed and the scope of the terms used herein is intended to include all such new technologies a priori.

As used herein the term "about" refers to ±10%

The phrase Operatively connected', as used herein, equivalency refers to the corresponding synonymous phrases Operatively joined', and 'operatively attached', where the operative connection, operative joint or operative attachment, is according to a physical, or/and electrical, or/and electronic, or/and mechanical, or/and electro-mechanical, manner or nature, involving various types and kinds of hardware or/and software equipment and components.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of expanding a prostatic urethra comprising:
    inserting a collapsed implant into the prostatic urethra the implant including a distal retractor connecting between a central ridge and two peripheral ridges, said peripheral ridges on opposing lateral sides of said central ridge and a proximal retractor;
    orienting said implant in the prostatic urethra with said distal retractor cranial to said proximal retractor;
    aligning said implant with said central ridge toward an anterior side of the prostatic urethra;
    positioning respective distal portions of each of said two peripheral ridges within the prostatic urethra proximal to a bladder neck thereof;
    opening said distal retractor to support and expand said respective distal portion of said two peripheral ridges within a cranial portion of the prostatic urethra on opposite posterior-lateral sides of said bladder neck;
    expanding lateral walls of a cranial portion of the prostatic urethra adjacent to the bladder neck;

resting at least one of said respective distal portions on an end of said cranial portion of the prostatic urethra to prevent migration of said implant into a urinary bladder;

opening said proximal retractor to support and expand lateral walls of a caudal portion of said prostatic urethra caudal to said cranial portion.

2. The method of claim 1, further comprising:

Supporting a wall of an intermediate portion of said prostatic urethra between said cranial portion and said caudal portion on an anterior side thereof by said central ridge and on a posterior side thereof by said two peripheral ridges wherein in said intermediate portion said two peripheral ridges have a closed form with at least a portion of a space between the two peripheral ridges and the central ridge being empty such that lateral walls of the urethra between the central ridge and the two peripheral ridges are unsupported.

3. The method of claim 2, further comprising:

supporting lateral walls of said cranial portion between said central ridge and said two peripheral ridges by said distal retractor.

4. The method of claim 1, wherein said implant is open between said two peripheral ridges on a posterior side of the prostatic urethra the method further comprising:

leaving said posterior side of the prostatic urethra unsupported during said opening of said proximal retractor and said opening of said distal retractor.

5. The method of claim 1, wherein said distal retractor is arc shaped and further comprising:

supporting lateral walls of said cranial portion with said distal retractor.

6. The method of claim 5, wherein said proximal retractor is arc shaped and further comprising:

supporting lateral walls of said caudal portion with said proximal retractor.

7. The method of claim 6, further comprising:

supporting a wall of an intermediate portion of said prostatic urethra between said cranial portion and said caudal portion is on an anterior side thereof by said central ridge and on a posterior side thereof by said two peripheral ridges wherein in said intermediate portion, the walls of the urethra between the central ridge and the peripheral ridges are unsupported.

8. The method of claim 7, wherein said implant is open on a posterior side of the prostatic urethra between said two peripheral ridges, said method further comprising:

leaving said posterior side of the prostatic urethra unsupported during said opening of said proximal retractor and said opening of said distal retractor.

9. The method of claim 1, further comprising aligning said central ridge with an anterior interlobar groove of said prostatic urethra.

10. The method of claim 9, wherein aligning comprises transferring a torque applied to a manipulator connected to the implant.

11. The method of claim 1, further comprising: connecting a manipulator to said proximal retractor.

12. The method of claim 11, further comprising causing the implant to laterally compress and retreat within a deployment lumen when an alignment or a position of the implant is incorrect.

13. The method of claim 12, wherein said causing includes pulling said manipulator proximally towards said deployment lumen.

14. The method of claim 13, further comprising detaching said manipulator from said proximal retractor.

15. The method of claim 13, wherein said connecting is to two caudolateral corners of the proximal retractor.

16. The method of claim 1, wherein said opening said distal retractor and opening said proximal retractor are sequential.

\* \* \* \* \*